United States Patent [19]

Koga et al.

[11] Patent Number: 5,075,296
[45] Date of Patent: Dec. 24, 1991

[54] AZACYCLOOCTADIENE COMPOUND AND PHARMACEUTICAL USE

[75] Inventors: Kenji Koga; Kiyoshi Tomioka; Yoshihiro Kubota, all of Tokyo; Makoto Asada; Kyosuke Kitoh, both of Ibaraki, all of Japan

[73] Assignee: Eisai Co., Ltd., Tokyo, Japan

[21] Appl. No.: 484,101

[22] Filed: Feb. 23, 1990

[30] Foreign Application Priority Data

Mar. 3, 1989 [JP] Japan ................................ 1-51225

[51] Int. Cl.$^5$ .................... A61K 31/33; C07D 498/22
[52] U.S. Cl. .................................. 514/183; 540/476
[58] Field of Search ........................ 540/476; 514/183

[56] References Cited

PUBLICATIONS

Devita et al., "Cancer . . . " S. B. Lippincott Co: (1985).
Tomioka et al., "Design, Synthesis and Antitamar . . ." Tetrahedron Lett. 30(22)2949-2952 (1989).

Primary Examiner—C. Warren Ivy
Assistant Examiner—Celia Chang
Attorney, Agent, or Firm—Flynn, Thiel, Boutell & Tanis

[57] ABSTRACT

An azacyclooctadiene compound having the formula (1) or a pharmacologically acceptable salt thereof is novel and useful as an anti-tumor agent.

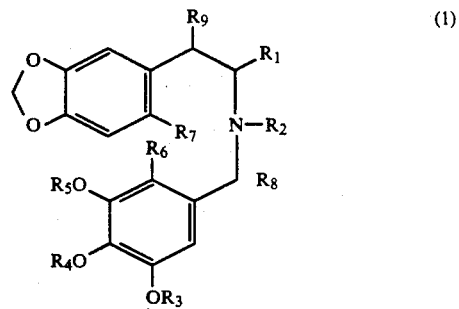

(1)

in which $R_1$ is —$CH_2R$, R being hydrogen, —$COCH_3$, —OH, —$NH_2$, —COOH or —$OCOCH_3$, or may form —$CH_2$—X—Y— together with $R_2$; $R_2$ is hydrogen, an alkyl having 1 to 4 carbon atoms or —$COR_{10}$, $R_{10}$ being hydrogen, an alkyl having 1 to 4 carbon atoms, —$OR_{11}$ or —$NHR_{11}$, $R_{11}$ being an alkyl having 1 to 4 carbon atoms, or may form —$CH_2$—X—Y— together with $R_1$; $R_3$, $R_4$ and $R_5$ each are hydrogen or methyl; $R_6$ and $R_7$ each are hydrogen or may form the direct bond to each other; $R_8$ is hydrogen or may form the direct bond to $R_7$; and $R_9$ is hydrogen, —$N_3$, —$NH_2$, —$OCH_3$ or =0; X being oxygen or —NZ—, Z being hydrogen, methyl, —$COCH_3$, —$CH_2COOH$, —CO—CH=$CH_2$, —CO—CH=CH—$CH_3$, —$CH_2C_6H_5$, —$CH_2OH$, —$CH_2OCOCH_3$ or —$CH_2$—COOC(CH$_3$)$_3$, Y being —SC—, —CO— or —$CH_2$—.

5 Claims, No Drawings

AZACYCLOOCTADIENE COMPOUND AND PHARMACEUTICAL USE

The present invention relates to new azacyclooctadien derivatives and acid addition salts thereof and an antitumor agent containing at least one of these compounds as the active ingredient.

PRIOR ART

Various chemotherapeutic agents for the treatment of a cancer have been developed and, for example, alkylating agents and antimetabolites are used for this purpose.

Etoposide and derivatives thereof were already commercialized and are available on the market.

Further di- and tetrahydroisoquinoline derivatives were reported as new compounds having an antitumor action (see Japanese Patent Laid-Open No. 283960/1987).

However, no quite satisfactory antitumor agents have been found as yet.

SUMMARY OF THE INVENTION

After intensive investigations made for the purpose of finding substances having an excellent antitumor activity, the inventors have found that new azacyclooctadiene derivatives and acid addition salts thereof have an excellent antitumor activity. The present invention has been completed on the basis of this finding.

Thus the present invention provides azacyclooctadiene derivatives of the general formula (1):

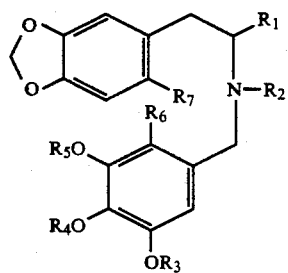

wherein $R_1$ represents a group of the formula: $-CH_2R$ (where R is $-H$, $-COCH_3$, $-OH$, $-NH_2$, $-COOH$ or $-OCOCH_3$) or $R_1$ is combined with $R_2$ to form $-CH_2-X-Y$ [where X is $-O-$ or

Z is $-H$, $-CH_3$, $-COCH_3$, $-CH_2COOH$, $-CO-CH=CH_2$, $-CO-CH=CH-CH_3$, $-CH_2C_6H_5$, $-CH_2OH$, $-CH_2OCOCH_3$ or $-CH_2COO-C(CH_3)_3$, and Y is

or $-CH_2-$], $R_2$ represents $-H$, an alkyl group having 1 to 4 carbon atoms or $-CHO$, or $R_2$ is combined with $R_1$ to form a group of the above-mentioned formula: $-CH_2-X-Y$, $R_3$, $R_4$ and $R_5$ each represent $-H$ or $-CH_3$, and $R_6$ and $R_7$ represent $-H$ or $R_6$ and $R_7$ are combined together to form a direct bond, and acid addition salts thereof, and antitumor agents containing at least one of these compounds as the active ingredient.

The azacyclooctadiene compound of the invention is defined by the formula (1). A pharmacologically acceptable salt of the compound falls within the invention. It is novel and useful as an anti-tumor agent. In the formula (1) $R_1$ is $-CH_2R$, R being hydrogen, $-COCH_3$, $-OH$, $-NH_2$, $-COOH$ or $-OCOCH_3$, or may form $-CH_2-X-Y-$ together with $R_2$; $R_2$ is hydrogen, an alkyl having 1 to 4 carbon atoms or $-COR_{10}$, $R_{10}$ being hydrogen, and alkyl having 1 to 4 carbon atoms, $-OR_{11}$ or $-NHR_{11}$, $R_{11}$ being an alkyl having 1 to 4 carbon atoms, or may form $-CH_2-X-Y-$ together with $R_1$; $R_3$, $R_4$ and $R_5$ each are hydrogen or methyl; $R_6$ and $R_7$ each are hydrogen or may form the direct bond to each other; $R_8$ is hydrogen or may form the direct bond to $R_7$; and $R_9$ is hydrogen, $-N_3$, $-NH_2$, $-OCH_3$ or $=O$; X being oxygen or $-NZ-$, Z being hydrogen, methyl, $-COCH_3$, $-CH_2COOH$, $-CO-CH=CH_2$, $-CO-CH=CH-CH_3$, $-CH_2C_6H_5$, $-CH_2OH$, $-CH_2OCOCH_3$ or $-CH_2-COOC(CH_3)_3$, Y being $-CS-$, $-CO-$ or $-CH_2-$.

Some preferable embodiments of the invention are the azacyclooctadiene compound having the formula (2) in which $R_6$ and $R_7$ form the direct bond to each other; $R_1$ and $R_2$ form $-CH_2-X-CO-$; $R_8$ is hydrogen; and $R_9$ is hydrogen; the azacyclooctadiene compound having the formula (3) in which $R_6$ and $R_7$ form the direct bond to each other; $R_8$ is hydrogen; and $R_9$ is hydrogen; the azacyclooctadiene compound having the formula (4) in which $R_1$ and $R_2$ form $-CH_2-X-CO-$; and $R_6$, $R_7$, $R_8$ and $R_9$ are hydrogen; and the azacyclooctadiene compound having the formula (5) in which $R_1$ and $R_2$ form $-CH_2-X-CO-$; $R_7$ and $R_8$ form the direct bond to each other; and $R_6$ is hydrogen.

The invention provides a pharmacological composition which comprises a therapeutically effective amount of the azacyclooctadiene compound or the pharmacologically acceptable salt thereof as defined above and a pharmacologically acceptable carrier and then to the pharmacological use of the compound or its salt as an anti-tumor agent.

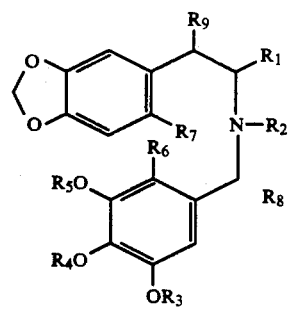

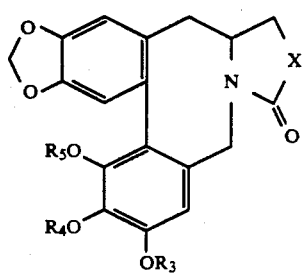

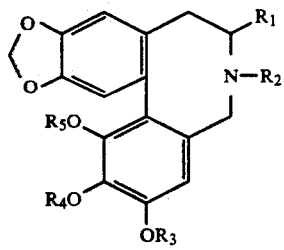

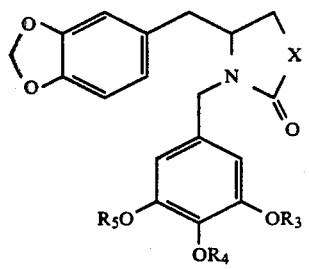

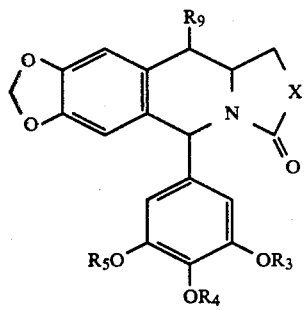

With one or more asymmetric carbon atoms, causing optical activity, in the compound of the formula (1), separate enantiomers and their mixtures are included in the present invention. Further the respective stereoisomers and their mixtures are also included in the present invention.

The acids capable of forming pharmacologically acceptable acid addition salts of the compounds of the formula (1) in the present invention are, for example, hydrochloric acid, sulfuric acid, phosphoric acid, nitric acid and organic acids such as citric, fumaric, maleic, tartaric, acetic, benzoic, p-toluenesulfonic, methanesulfonic and naphthalene-sulfonic acids.

Preferred examples of the compounds of the formula (1) in the present invention include azacyclooctadiene derivatives of the following formulae (2), (3) and (4) and acid addition salts thereof:

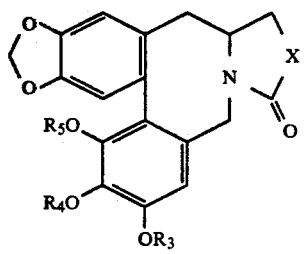

wherein $R_3$, $R_4$ and $R_5$ each represent —H or —CH$_3$, X represents —O— or

and Z represents —H, —CH$_3$, —COCH$_3$, —CH$_2$COOH, —CO—CH=CH$_2$, —CO—CH=CH—CH$_3$, —CH$_2$C$_6$H$_5$, —CH$_2$OH, —CH$_2$OCOCH$_3$ or —CH$_2$COO—C(CH$_3$)$_3$,

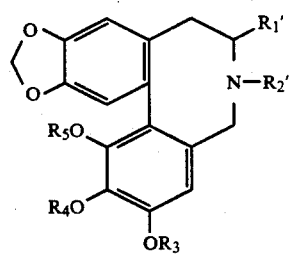

wherein
$R_1'$ represents —CH$_2$OH, —CH$_2$OCOCH$_3$ or —CH$_2$COOH,
$R_2'$ represents —CH$_3$ or —CHO, and
$R_3$, $R_4$ and $R_5$ each represent —H or —CH$_3$, and

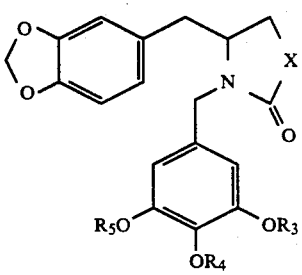

wherein X represents —O— or

(where Z' is —H or —CH$_2$C$_6$H$_5$), and
$R_3$, $R_4$ and $R_5$ each represent —H or —CH$_3$.

The new azacyclooctadiene derivatives and acid addition salts thereof according to the present invention can be prepared by any of the following processes A to D.

When the configuration of the biphenyl portion of the compound of the present invention is as shown in the following formulae, compound (a) has an α-hydrogen atom [

in the following formula (a)] at the 8-position of the azacyclooctadiene and compound (b) has a β-hydrogen atom [

in the following formula (b)] at the 8-position thereof:

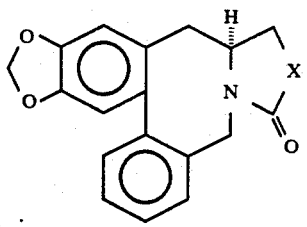 (a)
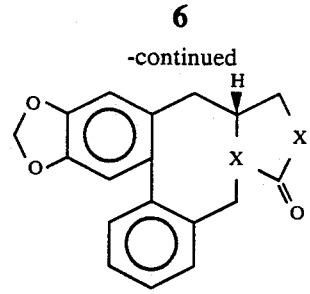 (b)
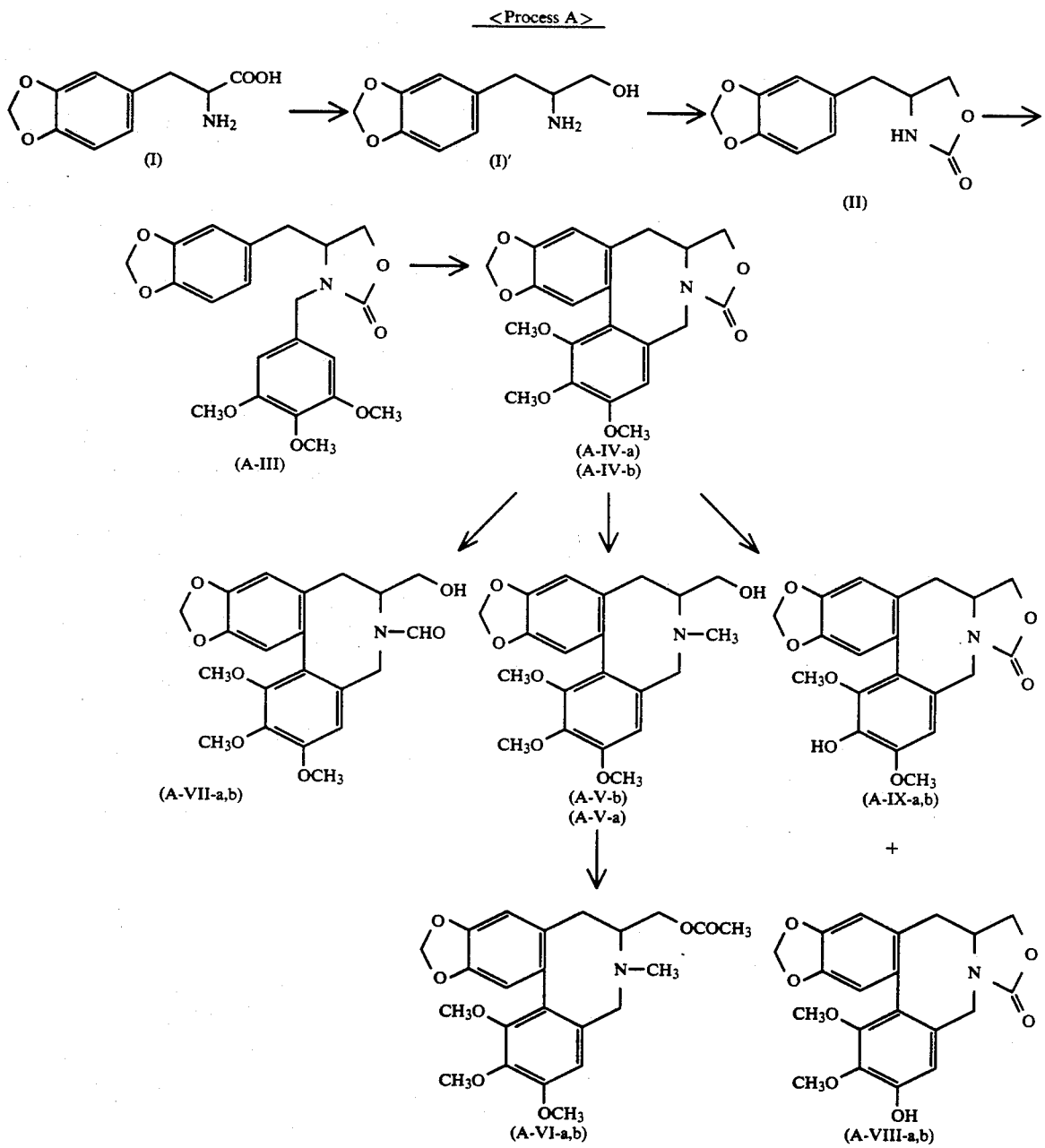
The process A will now be described in detail.
The starting compound (I) of the present invention is prepared by a known process [see S. Yamada et al., Chem. Pharm. Bull. (Japan) 10, 680 (1962)]. It is hydrogenated with LiAlH₄ in tetrahydrofuran (THF). Diethyl carbonate is added thereto in anhydrous ethanol to form a urethane compound (II).

The compound (II) is dissolved in anhydrous THF and NaH is suspended in the solution 3,4,5-Trimethoxybenzyl bromide prepared by a known process [see Michizo Asano et al., Yakugaku Zasshi (J. Pharm. Soc. Japan), 60, 105 (1940)] is added to the suspension and the mixture is heated under reflux for 3 h to obtain a compound (A-III).

Then a solution of $VOF_3$ in a mixture of trifluoroacetic acid and methylene chloride is cooled to −42° C. and the compound (A-III) is added thereto. The mixture is stirred at −42° C. to effect ring closure. After extraction with methylene chloride, compounds A-IV-a and A-IV-b are obtained.

After purification by to silica gel chromatography, the compound A-IV-a is obtained as colorless, acicular or needle crystals and the compound A-IV-b is obtained as colorless prisms. The compounds A-IV-a and A-IV-b can be formed reversibly by stirring them in an argon gas stream at 180° C. for 3 h.

The urethane bond of the compound A-IV-b is cleaved to cause ring opening with $LiAlH_4$ in THF to thereby form a compound A-V-b. The compound (A-IV-a) similarly undergoes ring opening to form a compound (A-VII-a).

The methoxy group of the compound (A-IV-b) can be selectively converted into an alcoholic group to form compounds (A-VIII-b) and (A-IX-b) by adding a solution of HBr in methylene chloride thereto and conducting a reaction at 0° C. for 7 h or by adding 1,2-dichloroethane thereto and saturating the mixture with HBr gas under stirring at 0° C. in an ordinary manner.

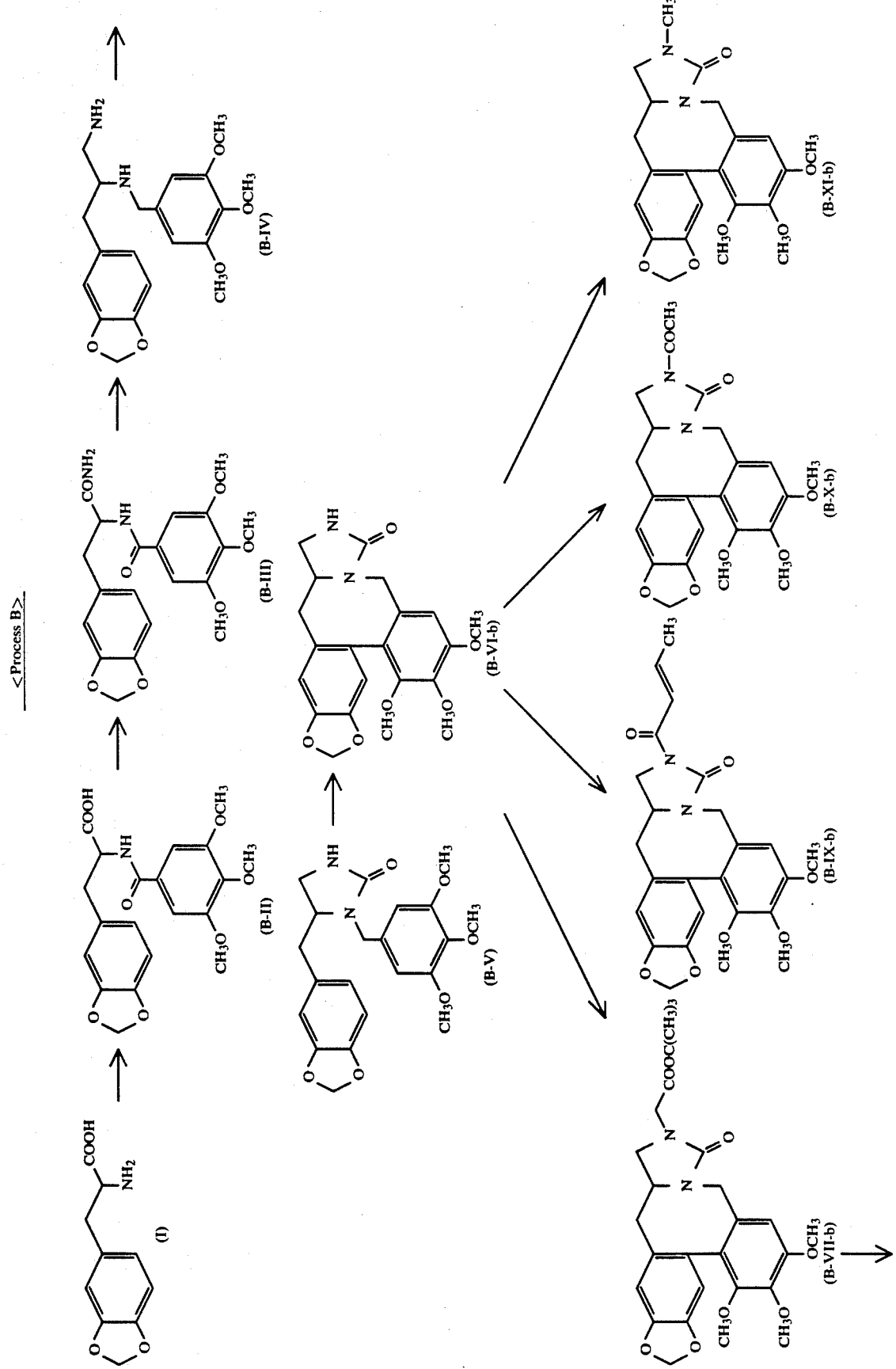

-continued
<Process B>
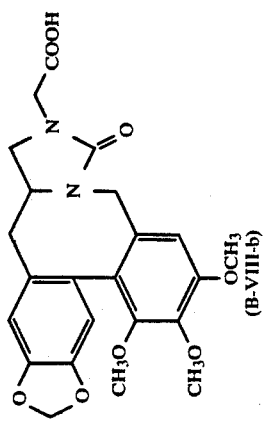
(B-VIII-b)

The process B will now be described in detail.

The compound (I) is dissolved in a 1N NaOH solution and 3,4,5-trimethoxybenzoyl chloride is added thereto at 0° C. The mixture is stirred at room temperature for 17 h to cause a direct reaction to thereby give a compound (B-II).

The compound (B-II) is placed in a solution of ethyl chloroformate in chloroform and triethylamine is added to the solution at −30° C. and stirred. Then gaseous NH₃ was introduced thereinto at 0° C. to convert the carboxylic acid group in the side chain into the corresponding amide group to thereby obtain a compound (B-III). It is converted into an amino compound (B-IV) in an ordinary manner. Diethyl carbonate is added thereto in ethyl alcohol and ring closure is effected by heating the mixture under reflux to obtain a urea compound (B-V). The compound (B-V) undergoes ring closure with VOF₃ to give a compound (B-VI-b).

The amine portion of the compound (B-VI-b) is reacted with BrCH₂COOC(CH₃)₃ in the presence of NaH to give a compound (B-VII-b). Further, a carboxylic acid compound (B-VIII-b) can be obtained in the presence of CF₃COOH.

The compound (B-Vi-b) can be reacted with CH₃COCl in the presence of NaH to give a compound (B-X-b).

A solution of n-BuLi in hexane is added to the compound B-VI-b in THF at −78° C. Dimethoxyethane is added and then crotonyl chloride is added at −78° C. to conduct a reaction to thereby give a compound (B-IX-b).

NaH is added to the compound (B-VI-b) in THF solvent and CH₃I is added thereto after cooling. The mixture is stirred under reflux at 50° C. to give a compound (B-XI-b).

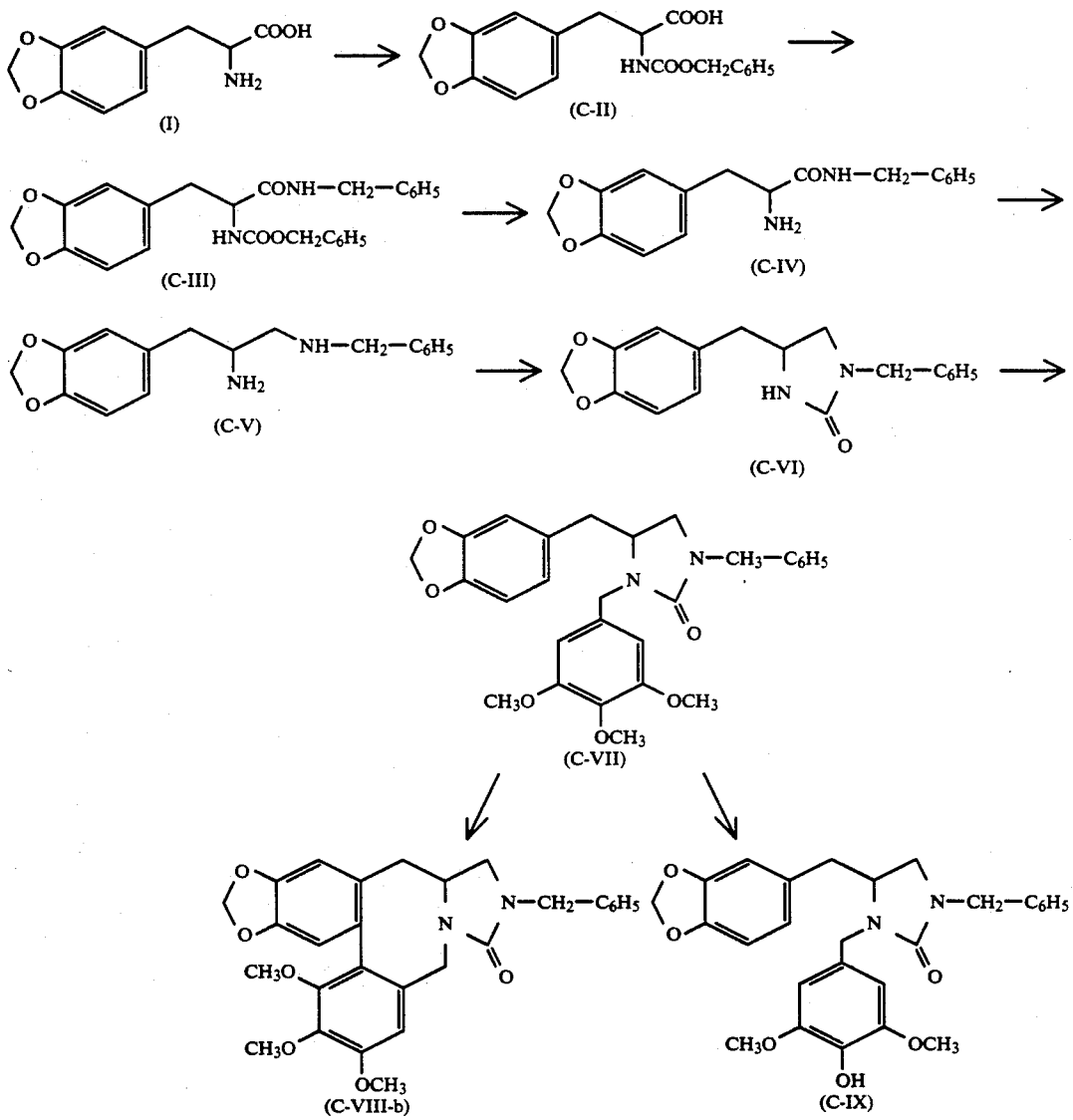

<Process C>

The process C will now be described in detail.

Benzyloxycarbonyl chloride is added to the compound (I) in the presence of an alkali and stirred at 0° C. The aqueous layer is acidified with concentrated hydrochloric acid. After extraction with ethyl acetate, a compound (C-II) is obtained.

A solution of triethylamine in methylene chloride is stirred at 0° C. and isobutyl chloroformate is added to conduct a reaction. A solution of benzylamine in CH$_2$Cl$_2$ is added dropwise thereto and stirred at room temperature for 2 h to give a compound (C-III).

Then a 25% HBr/CH$_3$COOH solution is added thereto to conduct a reaction at room temperature to thereby give an amide compound (C-IV).

LiAlH$_4$ is added to the amide in THF to conduct a reaction under stirring under reflux to give a compound (C-V) as a yellow oily substance.

Then metallic sodium is added to anhydrous ethanol. After metallic sodium has disappeared, the diamine and a solution of diethyl carbonate in ethanol are added thereto. They are stirred and the pH of the mixture is adjusted to 1 with 10% HCl. A compound (C-VI) is obtained by extraction with CH$_2$Cl$_2$.

Then, 3,4,5-trimethoxybenzyl bromide is added in the same manner as that of the process A to give a compound (C-VII).

After the ring closure is conducted in a solution of VOF$_3$ in CF$_3$COOH and CH$_2$Cl$_2$ at −42° C., a compound (C-VIII-b) is obtained.

A solution of NaI in CH$_3$CN is added to the urea compound (C-VII), and then, trimethylsilyl chloride (TMSCl) is added thereto to conduct a reaction at room temperature to partially convert the methoxy group into a hydroxy group to thereby form a compound (C-IX).

The process D for preparation is described below. 3,4,5-trimethoxybenzaldehyde, obtained by the disclosure in Asano et al., Yakugaku Zasshi(pharmacoloy magazine), 60, 105(1942), and CF3COOH are added to a benzene solution of the compound (II). The mixture is refluxed for 120 hours to obtain the compound D-I in the trans form D-I-a and the cis form D-I-b. The trans compound D-I-a is dissolved in 1,2-dichloroethane. The solution is saturated with hydrogen bromide gas and then stirred at zero degree centigrade for 14 hours to obtain the compounds D-II and D-II', which are shown below stereochemically in their chemical formulae.

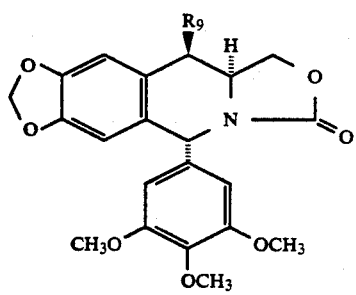

(a)

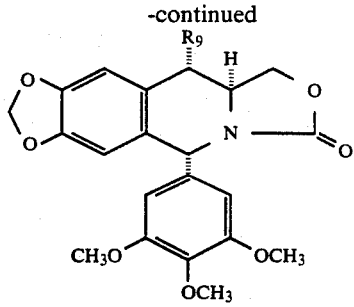

(b)

The urethane form of the comound (II) is heated and stirred in an acetic acid suspension or dispersion of 2,3-dichloro-5,6-dicyano-1,4-benzoquinone at 60 degree centigrade for 50 hours to obtain the compound D-III, according to the disclosure of K. Tomioka et al. J. Chem. Soc., Chem. Commun 1989, 1622. This is dissolved in methanol and sodium hydrogen carbonate is added thereto. The solution is stirred at room temperature for 3 hours to obtain the compound D-IV in the alcohol form. This is chlorinated with a concentrated hydrochloric acid to obtain the compound D-V. This is stirred with a dimethylformamide suspension of potassium phthalic imide at room temperature for 30 mins. and then at 40 degree centigrade for 30 minutes to obtain the compound D-VI. The compounds D-VI-a and D-VI-b are obtained by separation and purification with column chromatography.

Then, the compound D-VI and 3,4,5-trimethoxybenzaldehyde are dissolved in a solvent mixture of methylene chloride and methanol. Trifluoromethane sulfonic acid is added thereto. The solution is stirred at room temperature for 22 hours and a saturated sodium hydrogen carbonate solution is added thereto. The solution is stirred for 10 minutes to obtain the compound D-VII. This compound and hydrazine hydrate are suspended in a solvent mixture of methanol and chloroform and the suspension is refluxed with stirring for 2 hours. After concentration, the residue was refluxed for 2 hours in 2N-hydrochloric acid and ethanol to obtain the compound D-XI in the amine form.

The compound D-XI can be obained another way. The compound D-V is dissolved in a dimethylformamide suspension of NaN3 and the suspension is stirred at 70 degree centigrade for 11 hours to obtain the compound D-IX. This compound is ring-closed with 3,4,5-trimethoxybenzaldehyde to obtain the compound D-X in the azide form. This is stirred in ethanol with a catalyst in hydrogen gas at zero degree centigrade for 6 hours to obtain the compound D-XI in the amino form.

Separately the compound D-IX is obtained by dissolving the compound D-IV in a 15% hydrochloric acid in methanol, stirring and refluxing the solution for 1 hour to obtain the compound D-VIII in the methoxy form, adding to the compound D-VIII a methylene chloride solution of trimethylsilyl azide (CH3)3SiN3, stirring the mixture, ice-cooled, with addition of trimethylsilyl triflate CF3SO3Si(CH3)3, then stirring the mixture at room temperature for 24 hours, allowing it to cool, adding KF thereto and a saturated sodium hydrogen carbonate and stirring it for 30 minutes.

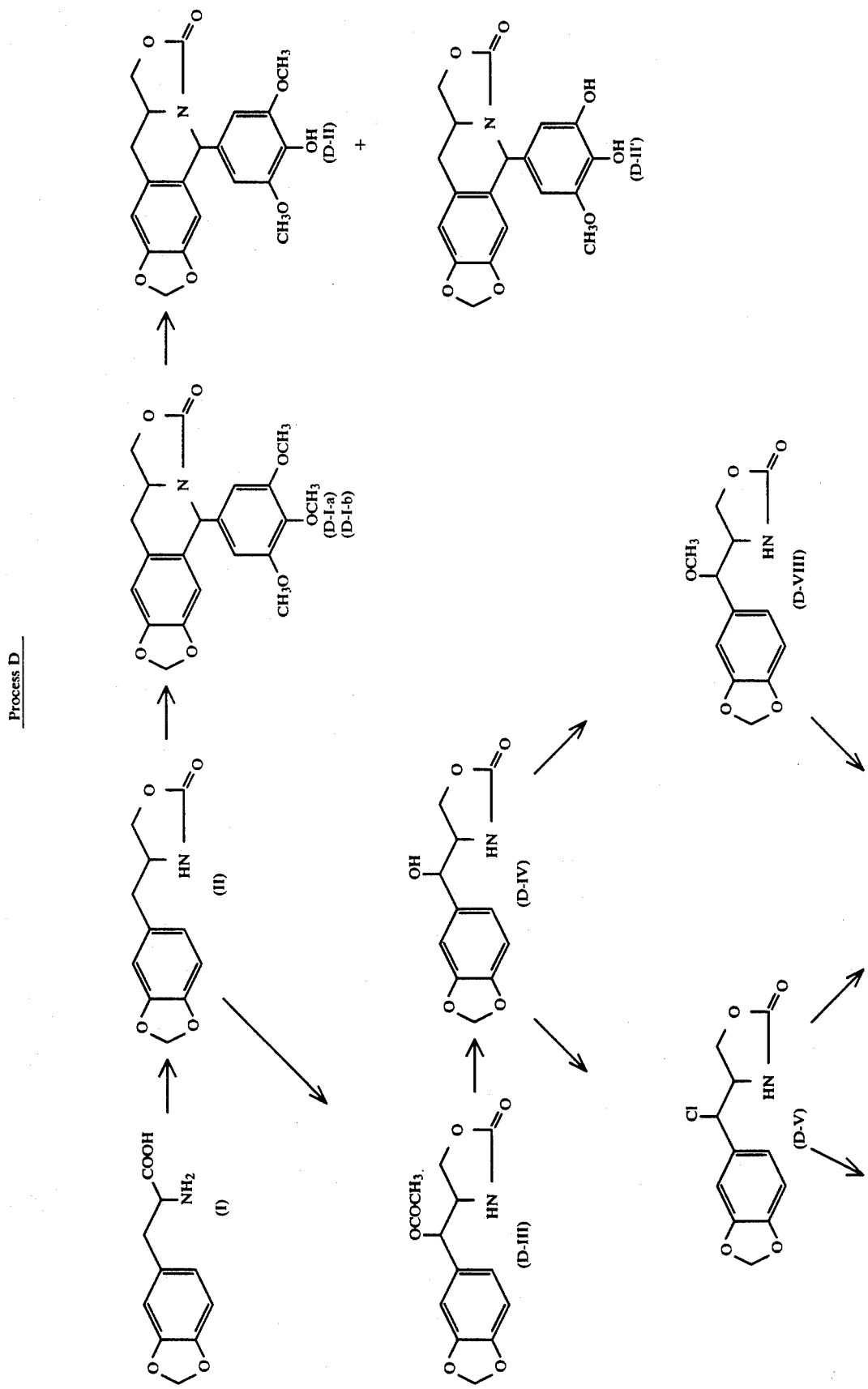
Process D

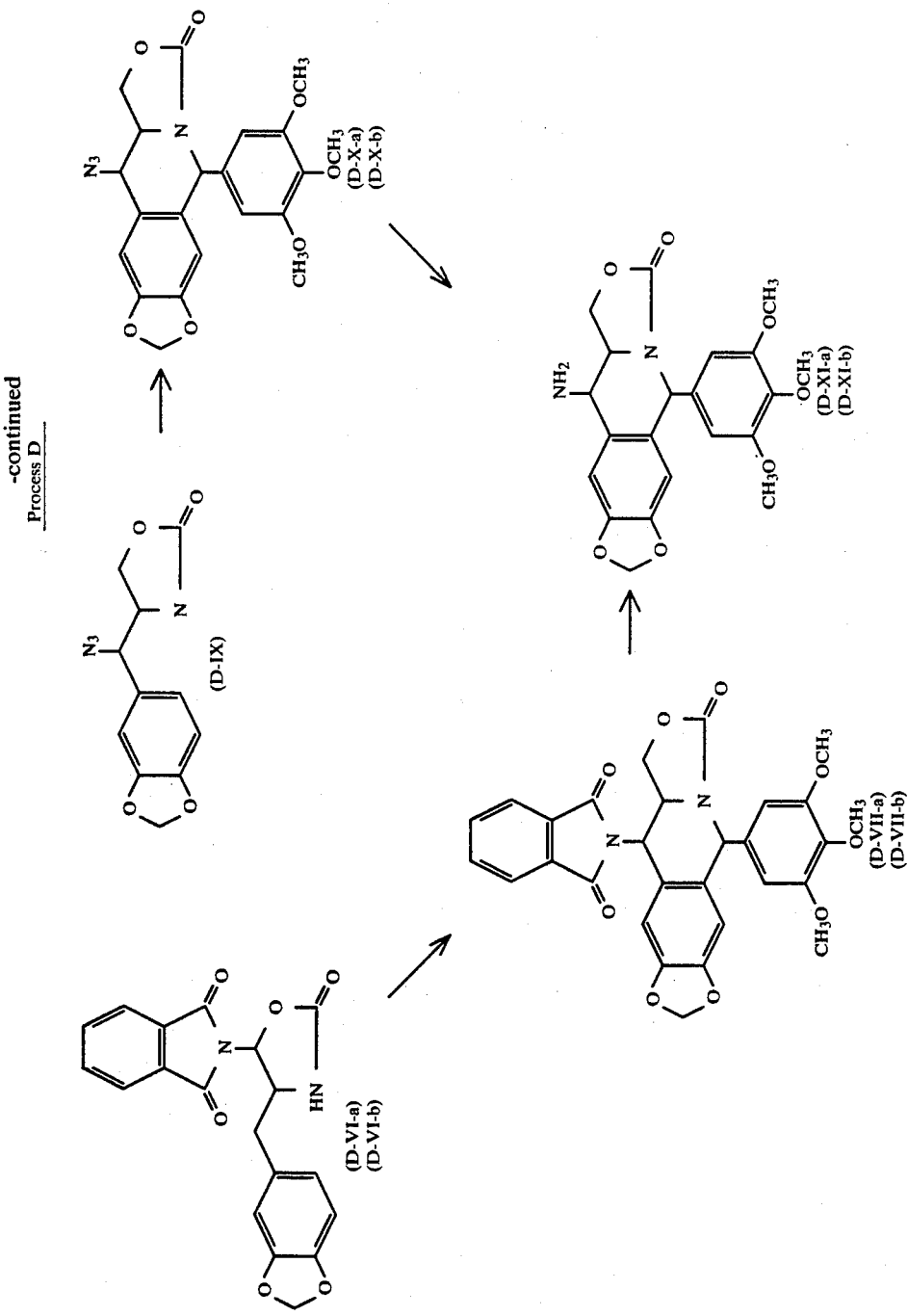

The antitumor activity of the compounds of the present invention was determined in vitro with cultured KB cells.

EXPERIMENT I

The experiment was conducted by using KB derived from a human epidermoid carcinoma of the mouth and Eagle's minimal essential medium (MEM) - 10% calf serum at 37° C. in a carbon dioxide incubator (5% $CO_2$).

KB cells were diluted at a dilution rate of $1 \times 10^4$/ml medium. 2 ml of the sample thus formed was placed in a 30-mm plastic dish so that the final concentration of the compounds of the present invention would be 100, 30, 10, 3 or 1 μg/ml. After four days, the cells were peeled from the dish surface with trypsin and the number of the cells was counted with a Coulter counter.

The criterion according to NCI (U.S.A.) was employed to determine the concentration ($ED_{50}$) at which the growth inhibition was substantially 50% based on the control. Compounds having an $ED_{50}$ value of 4 μg/ml or below was regarded to be effective.

The results are shown in Table 1.

TABLE 1

| Compound No. | $ED_{50}$ (μg/ml) |
| --- | --- |
| A-III | 35.0 |
| A-IV-a | 47.0 |
| A-IV-b | <0.3 |
| A-V-a | 1.5 |
| A-V-b | 1.1 |
| A-VI-a | 1.65 |
| A-VII-a | <0.3 |
| A-VIII-a | 17 |
| A-IX-a | 50 |
| B-V | 47.0 |
| B-VI-b | <0.3 |
| B-VII-b | 1.7 |
| B-VIII-b | 5.4 |
| C-VII | 16.5 |
| D-X-a | 0.68 |
| D-X-b | <0.3 |
| D-XI-b | <0.3 |
| D-XI-a | <0.3 |

It is apparent from the results of the above-described pharmacological experiments that the compounds of the present invention have an antitumor effect and are usable as preferred antitumor agents.

When the compounds of the present invention are used as medicine, they are given by either oral or parenteral administration. The dose is not particularly limited, since it varies depending on the degree of the symptoms; age, sex, body weight and sensitivity of the patient; administration method; period and time interval of the administration; properties; formulation and kind of medical preparation; and kind of active ingredient.

In the preparation of a solid medicine for the oral administration, an excipient and, if necessary, a binder, disintegrator, lubricant, colorant, corrigent, etc. are added to the active ingredient and the mixture thus obtained is shaped into pills, tablets, coated tablets, powder, granules, dust or capsules by an ordinary method.

EXPERIMENT II

Female ICR mice being 6 weeks old were inoculated abdominally with 0.2 ml of a sample of cell suspension in PBS containing $5 \times 10^5$ S-180 salcoma cells, on Day 0. Once a day for 5 days (Day 1 to 5) from the next day, they were inoculated abdominally with the above shown compounds of A-IV-b, B-VI-6 and D-I-a, respectively, dispersed in 6 wt. % dimethylsulfoxide solution, with intra-peritoneal injection of 25 or 50 mg/kg. A saline and a solvent were used for reference control. 12 to 7 mice were used in the saline control and the drug test, respectively. Antitumor activity was determined by the mean survival time (prolongation of life) of the test group (T) with that of the control group (C) and is shown in terms of an increase in life-span (prolongation extent of life), that is, $((T/C) \times 100\%)$. The observation period was 52 days and survivors were excluded from calculation.

| group | Average days of the prolongation of life | Prolongation extent of life (%) | Number of surviving mice |
| --- | --- | --- | --- |
| control | | | |
| (saline) | 13.3 ± 3.7 | 0 | 0/12 |
| (DMSO) | 12.0 ± 3.0 | −11 | 0/7 |
| A-IV-b | | | |
| 25 mg/kg | 12.9 ± 2.3 | −4 | 0/7 |
| 50 | 19.0 ± 5.5 | 40 | 0/7 |
| B-VI-b | | | |
| 25 mg/kg | 20.2 ± 4.2 | 50 | 2/7 |
| 50 | 29.7 ± 3.9 | 120 | 0/7 |
| D-I-a | | | |
| 25 mg/kg | 21.9 ± 4.0 | 62 | 0/7 |
| 50 | 20.0 ± 5.6 | 48 | 0/7 |

EXAMPLE 1

[Preparation of compound (II)]

46.8 g (0.19 mol) of hydrochloride of the compound (I) was added to 1.3 l of tetrahydrofuran (THF), in which 29.0 g (0.76 mol) of $LiAlH_4$ had been suspended, under stirring at room temperature and the mixture was stirred under reflux for 3 h. The mixture was cooled to room temperature and then 29 ml of $H_2O$, 29 ml of 15% sodium hydroxide and 87 ml of $H_2O$ were successively added thereto. The mixture was stirred at room temperature for 20 min and an insoluble matter was filtered by means of suction through a glass filter.

The insoluble matter was washed with 200 ml of THF and the THF solution was concentrated under reduced pressure to give 36.3 g (yield: 98%) of crude crystals of the amino alcohol compound (I'). This product was recrystallized from 50 ml of benzene to give 25.8 g of colorless acicular crystals (yield: 70%).

100 ml of anhydrous ethanol was added to 25.6 g (131 mmol) of the product and then 0.3 g (13 mmol) of Na was added thereto. After the Na had disappeared, 159 ml (1.31 mol) of diethyl carbonate was added thereto and the mixture was stirred under reflux for 4 h.

After cooling followed by concentration under reduced pressure, 50 ml of 10% hydrochloric acid was added to the concentrate. The product was extracted with 200 ml of ethyl acetate three times.

The ethyl acetate layer was washed with 160 ml of a saturated sodium hydrogencarbonate solution and 160 ml of a saturated aqueous common salt solution and dried with sodium sulfate. The crude product, concentrated, and recrystallized from 15 ml of ethyl acetate and ether (1:6), to gave 25.7 g of colorless prismatic crystals of the urethane compound (II) (yield: 89%).

EXAMPLE 2

[Preparation of compound (A-III)]

42 mg (1.09 mmol) of NaH (60% suspension) was added to 4 ml of a solution of 200 mg (0.90 mmol) of the urethane compound (II) in anhydrous THF and the mixture was stirred under reflux for two hours. After cooling, 2 ml of a solution of 283 mg (1.09 mmol) of 3,4,5-trimethoxybenzyl bromide in THF was added to the white dispersion thus obtained and the mixture was stirred under reflux for 3 h. 5 ml of a saturated $NH_4Cl$ solution, was added thereto and, after extraction with 20 ml of ethyl acetate three times, the combined ethyl acetate layers were washed with 10 ml of 10% HCl, 10 ml of a saturated $NaHCO_3$ solution and 10 ml of a saturated aqueous common salt solution successively. After drying over $Na_2SO_4$, followed by concentration under reduced pressure, 0.48 g of an oil thus obtained was purified according to silica gel chromatography [$SiO_2$, Fuji Gel BW-200 25 g, benzene-acetone (10:1)] to give 0.35 g (yield: 96%) of the compound (A-III) in the form of a colorless caramel. It was crystallized from ethyl acetate / n-hexane (1:6) to give 0.33 g (yield: 91%) of colorless platy crystals.

EXAMPLE 3

[Preparation of compound (A-IV-a) and compound (A-IV-b)]

A solution of 1.85 g (14.9 mmol) of $VOF_3$ in a mixture of 12 ml of trifluoroacetic acid and 120 ml of methylene chloride was cooled to $-42°$ C. and 96 ml of a solution of 2.00 g (4.98 mmol) of a urethane compound (A-III) in methylene chloride was added to the solution over 10 min. The mixture was stirred at $-42°$ C. for 3 h and then 70 ml of a saturated $Na_2CO_3$ solution was added thereto. The organic layer was separated and the aqueous layer was subjected to extraction with 100 ml of methylene chloride three times. The combined organic layers were washed with 160 ml of 10% HCl, 160 ml of a saturated $NaHCO_3$ solution and 200 ml of a saturated aqueous common salt solution successively and then dried. The organic layer thus treated was concentrated under reduced pressure to give 2.19 g of a pale yellow glass, which was purified according to silica gel chromatography [$SiO_2$, 200 g of Fuji Gel BW-200, n-hexane/benzene/acetone (5:5:2)] to give 1.91 g (yield: 96%) of compound (A-IV-b) in the form of colorless prismatic crystals (m.p.: 185° to 186° C.) and 48.1 mg (yield: 2.4%) of compound (A-IV-a) in the form of colorless acicular crystals (m.p.: 163° to 165° C.).

The compound (A-IV-b) was recrystallized from 50 ml of benzene/ether (1:4) to give 1.68 g (yield: 84%) of colorless prismatic crystals.

The compound (A-IV-a) was recrystallized from ethyl acetate to give 28 mg (yield: 1.4%) of colorless acicular crystals.

5.2 mg of compound (A-IV-a) was stirred under heating at 180° C. in an argon stream for 3 h. After cooling, it was confirmed according to liquid chromatography that the ratio of the compound (A-IV-b) to compound (A-IV-a) was 40:1 [Waters, radial Pak cartridge silica: 5μ, ethyl acetate / n-hexane=3:1, 3.0 ml/min, U.V. 264 nm, compound (A-IV-b): 2.9 min (8.7 ml , compound (A-IV-a): 7.3 min (21.9 ml)].

According to NMR, it was confirmed that the ratio of compound (A-IV-b) to compound (A-IV-a) was 40:1.

EXAMPLE 4

[Preparation of compound (A-V-b)]

8 ml of a solution of 157 mg (0.39 mmol) of the compound (A-IV-b) in THF was added to a suspension of 39.0 mg 1.02 mmol) of $LiAlH_4$ in 2 ml of THF at room temperature and the mixture was stirred under reflux for 2 h. After cooling, 39 μl of $H_2O$ , 39 μl of 15% NaOH and 0.12 ml of $H_2O$ were successively added thereto and the resultant mixture was stirred at room temperature for 20 min. An insoluble matter was removed by filtration and the filtrate was concentrated under reduced pressure to give 144 mg of a colorless oil. It was purified according to alumina column chromatography (II-III, $CHCl_3$) to give 125 mg of compound (A-V-b) in the form of a white powder (m.p.: 85° to 90° C.). Yield: 82%. It was recrystallized from 2 ml of benzene/ n-hexane (1:1) to give 112 mg (yield: 74%) of compound (A-V-b) in the form of a white powder.

EXAMPLE 5

[Preparation of compound [A-VI b)]

8 μl (0.085 mmol) of acetic anhydride was added to 0.5 ml of a solution of 22.0 mg (0.057 mmol) of the alcohol compound (A-V-b) in pyridine at 0° C. and the mixture was stirred at 0° C. for 1 h and then at room temperature for 2 h. The mixture was successively diluted with 30 ml of chloroform and then washed with 20 ml of a saturated $CuSO_4$ solution three times, 10 ml of a saturated aqueous solution of common salt, 10 ml of a saturated $NaHCO_3$ solution and 20 ml of a saturated aqueous solution of common salt and then dried over $Na_2SO_4$. After concentration under reduced pressure, 26.9 mg of a pale yellow oil was obtained. It was purified according to silica gel column chromatography (ethyl acetate /n-hexane / chloroform =3:1:1) to give 22.3 mg (yield: 91%) of the compound (A-VI-b) in the form of a colorless oil. A part of the product was converted into its hydrochloride with concentrated hydrochloric acid and then recrystallized from ethyl acetate (16.6 mg free→12.0 mg) to give colorless acicular crystals (m.p.: 199° to 121° C.).

EXAMPLE 6

[Preparation of compound (A-VII-a) and compound (A-V-a)]

A solution of 12.2 mg (0.031 mmol) of the compound (A-IV-a) in 1 ml of THF was added to 1 ml of a suspension of 7.0 mg (0.183 mmol) of $LiAlH_4$ in THF and the resultant solution was stirred under reflux for 1.5 h. 7 μl of $H_2O$, 7 μl of 15% NaOH and 21 μl of $H_2O$ were successively added thereto and the mixture was stirred for 20 min. An insoluble matter was removed by filtration. After concentration under reduced pressure, 11.2 mg of a remaining oil was purified according to silica gel TLC (ethyl acetate/methanol=9:1) to give 1.6 mg (yield: 13%) of the N-formyl compound (A-VII-a) and 2.7 mg (yield: 23%) of the N—$CH_3$ compound (A-V-a).

EXAMPLE 7

[Preparation of compound (A-VIII-b) and compound (A-IX-b)]

A solution of 93.5 mg (0.234 mmol) of the urethane compound (A-IV-b) in 4 ml of 0.3 M $HBr/CH_2Cl_2$ was stirred at 0° C. for 72 h. The product was concentrated under reduced pressure and 121 mg of a purple oil thus obtained was purified according to silica gel TLC (chloroform/ethyl acetate=9:1) to give 56 mg (60% recovery) of the starting material, 4.3 mg (yield: 5%) of the compound (A-VIII-b) and 29.0 mg (yield: 32%) of the compound (A-IX-b).

EXAMPLE 8

[Preparation of compound (B-II)]

21.0 g (85.5 mmol) of hydrochloride of the compound (I) was dissolved in 171 ml of 1N NaOH and 21.7 g (94.0 mmol) of 3,4,5-trimethoxybenzoyl chloride and 86.0 ml of 1N NaOH were separately added dropwise thereto under stirring at 0° C. over 1 h. The mixture was stirred at room temperature for 17 h and washed with 100 ml of diethyl ether twice. The pH of the aqueous layer was adjusted to 1 with concentrated hydrochloric acid and the treated layer was subjected to extraction with 500 ml of chloroform/THF (10/1) three times. The combined organic layers were washed with 600 ml of a saturated aqueous solution of common salt and then dried over $Na_2SO_4$. After concentration under reduced pressure, 35.7 g of the compound (B-II) was obtained in the form of a light brown solid. The product was recrystallized from 85 ml of acetic acid to give 30.0 g (yield: 87%) of the compound (B-II) in the form of a white powder.

EXAMPLE 9

[Preparation of compound (B-III)]

1.87 g (4.6 mmol) of the compound (B-II) and 5 ml of a solution of 0.65 ml (4.6 mmol) of triethylamine in chloroform were added to a solution of 0.44 ml (4.6 mmol) of ethyl chloroformate in 5 ml of chloroform at $-30°$ C. and the resulting mixture was stirred at 0° C. for 2.5 h. Then gaseous $NH_3$ was introduced into the reaction mixture for 20 min and the solution was stirred at room temperature for 1 h. It was concentrated under reduced pressure and 10 ml of 10% HCl was added to the residue. The formed white solid was collected by filtration and washed with 10 ml of 10% HCl and then with 10 ml of water to give 1.79 g of the compound (B-III) in the form of a white powder (m.p.: 210° to 216° C.). It was recrystallized from 12 ml of acetic acid/water (5/1) to give 1.46 g (yield: 79%) of the compound (B-III) in the form of colorless pillar crystals (M.P.:218° to 220° C.).

EXAMPLE 10

[Preparation of compound (B-IV)]

80 ml (80 mmol) of a 1M $BH_3$/THF solution was added to 5.30 g (13.2 mmol) of the compound (B-III) and the solution was stirred under reflux for 3 h. 40 ml of methanol saturated with hydrochloric acid was added thereto under stirring while cooling with ice. After stirring for 20 min, 1 l of methanol was added thereto and the mixture was concentrated under reduced pressure. After the addition of an additional 1 l of methanol followed by reduced pressure concentration and addition of 20 ml of 10% NaOH, the product was extracted with 50 ml of benzene three times. The organic layer was washed with 20 ml of a saturated aqueous solution of common salt, dried over $K_2CO_3$ and concentrated under reduced pressure to give 4.74 g of a pale yellow oil. After purification according to silica gel column chromatography (chloroform/methanol=5:1), 4.54 g (yield: 92%) of the compound (B-IV) was obtained in the form of a colorless oil.

EXAMPLE 11

[Preparation of compound (B-V)]

0.21 g (9.13 mmol) of Na was added to 6 ml of anhydrous ethanol. After confirming the disappearance of Na, a solution of 3.50 g (9.34 mmol) of the compound (B-IV) in 4 ml of ethanol and 11.3 ml (93.4 mmol) of diethyl carbonate were added thereto and the mixture was stirred under reflux for 2.5 h. After concentration under reduced pressure, 20 ml of 10% HCl was added thereto. After extraction with 30 ml of ethyl acetate three times, the combined organic layers were washed with 20 ml of a saturated $NaHCO_3$ solution and 20 ml of a saturated aqueous common salt solution and then dried over $Na_2SO_4$. 3.74 g of a brown caramel obtained by concentration under reduced pressure, was purified by to silica gel column chromatography (n-hexane/acetone=1:1) to give 2.13 g (yield: 57%) of the urea compound (B-V).

EXAMPLE 12

[Preparation of compound (B-VI-b)]

470 mg (3.80 mmol) of $VOF_3$ was added to a mixture of 3 ml of $CF_3COOH$ and 6 ml of $CH_2Cl_2$ and a solution of 498 mg (1.24 mmol) of the urea compound (B-V) in 24 ml of $CH_2Cl_2$ was added thereto at $-42°$ C. The mixture stirred at $-42°$ C. for 5 h and then 30 ml of a saturated $Na_2CO_3$ solution was added thereto. The organic layer was separated and the aqueous layer was subjected to extraction with 30 ml of $CH_2Cl_2$ three times. The combined organic layers were successively washed with 30 ml of 10% HCl, 30 ml of a saturated $NaHCO_3$ solution and 40 ml of a saturated aqueous solution of common salt and then dried over $Na_2SO_4$. After concentration under reduced pressure, 460 mg of a light brown solid was obtained. It was purified by to silica gel column chromatography (n-hexane/acetone=3:4) to give 440 mg (yield: 89%) of compound (B-VI-b) in the form of colorless acicular crystals (m.p.: 230 to 233° C.). It was recrystallized from 16 ml of ethanol to give 328 mg (yield: 66%) of compound (B-VI-b) in the form of colorless acicular crystals.

EXAMPLE 13

[Preparation of compound (B-VII-b)]

A solution of 500 mg (1.28 mmol) of compound (B-VI-b) in 10 ml of THF was added to 56 mg (1.44 mmol) of NaH (60% suspension in oil) and the mixture was stirred under reflux for 40 min. After cooling, 0.25 ml (1.54 mmol) of t-butyl bromoacetate was added thereto and the mixture was stirred under reflux for 2 5 h. After cooling 10 ml of a saturated $NH_4Cl$ solution was added thereto and the mixture was subjected to extraction with 30 ml of ethyl acetate three times. The combined organic layers were successively washed with 40 ml of 10% HCl, 40 ml of a saturated $NaHCO_3$ solution and 40 ml of a saturated common salt solution dried over $Na_2SO_4$ and concentrated under reduced pressure to give 690 mg of a pale yellow solid. It was purified according to silica gel column chromatography (benzene/ethyl acetate=3:1) to give 566 mg (yield: 88%) of compound (B-VII-b) in the form of a colorless solid (m.p.: 102° to 105° C.). After recrystallization from 20 ml of diethyl ether / n-hexane (1:1), 522 mg (yield: 80%) of compound (B-VII-b) in the form of colorless acicular crystals was obtained.

EXAMPLE 14

[Preparation of compound (B-VIII-b)]

0.102 g (0.20 mmol) of the compound (B-VII-b) was dissolved in 1 ml of $CF_3COOH$ and the solution was stirred at room temperature for 30 min. After concentration under reduced pressure, 90.0 mg (yield: 99%) of a brown solid was obtained. It was recrystallized from 1 ml of acetic acid/water (5:1) to give 70.0 mg (yield: 77%) of compound (B-VIII-b) in the form of colorless prismatic crystals.

EXAMPLE 15

Preparation of compound (B—X-b)]

150 mg (3.80 mmol) of NaH (60% suspension) was washed with 5 ml of anhydrous hexane three times. A suspension of 1.01 g (2.54 mmol) of compound (B-VI-b) in 30 ml of THF was added thereto and the mixture was stirred at room temperature for 45 min. 0.22 ml (3.04 mmol) of acetyl chloride was added thereto and the mixture was stirred under reflux for 1.5 h. After cooling, 10 ml of a saturated $NH_4Cl$ solution was added to the mixture and the resulting solution was subjected to extraction with 30 ml of ethyl acetate three times. The combined organic layers were successively washed with 20 ml of 10% HCl, 20 ml of a saturated $NaHCO_3$ solution and 30 ml of a saturated aqueous solution of common salt and then dried over $Na_2SO_4$. The product was concentrated under reduced pressure to give 1.14 g of a pale yellow solid. It was purified by silica gel column chromatography (benzene / ethyl acetate=5:3) to give 1.03 g (yield: 92%) of compound (B-X-b) in the form of colorless prismatic or prisms crystals (m.p.: 197° to 198° C.). After recrystallization from 20 ml of ethyl acetate / n-hexane (1:1), 0.92 g of compound (B-X-b) in the form of colorless prismatic crystals was obtained.

EXAMPLE 16

[Preparation of compound (B-IX-b)]

0.33 ml (0.53 mmol) of a 1.57M solution of butyl lithium in hexane was added to a suspension of 175 mg (0.44 mmol) of the urea compound (B-VI-b) in 2 ml of THF at −78° C. and the resulting solution was stirred at room temperature for 2 h. 2 ml of dimethoxyethane was added thereto and then 0.046 ml (0.48 mmol) of crotonyl chloride was added thereto at −78° C. The reaction mixture was stirred at room temperature for 2 h. 5 ml of a saturated $NH_4Cl$ solution was added thereto and the mixture was subjected to extraction with 20 ml of ethyl acetate three times. The organic layers were combined together, washed with 10 ml of 10% HCl, 20 ml of a saturated $NaHCO_3$ solution and 20 ml of a saturated aqueous solution of common salt successively and dried with $Na_2SO_4$. It was concentrated at a reduced pressure to give 207 mg of a white solid, which was purified according to silica gel column chromatography (chloroform / ethyl acetate=6:1 and then chloroform / acetone=1:1) to give 84.4 mg (yield: 41%) of the N-acyl compound (B-IX-b) in the form of colorless prismatic crystals (m.p.: 236° to 240° C.). Then 107 mg (yield: 59%) of the starting urea compound was recovered. The N-acyl compound was recrystallized from 1 ml of ethyl acetate hexane (1:1) to give 69 mg of compound (B-IX-b) in the form of colorless prismatic crystals.

Example 17

[Preparation of compound (B—XI-b)]

20.0 mg (0.50 mmol) of NaH (60% suspension) was added to a suspension of 101 mg (0.254 mmol) of urea compound (B-VI-b) in 3 ml of THF and the mixture was stirred under reflux for 30 min. After cooling, 1.3 ml (20.9 mmol) of $CH_3I$ was added thereto and the solution was stirred under reflux at 50° C. for 2 h. After cooling, 10 ml of a saturated $NH_4Cl$ solution was added thereto and the mixture was subjected to extraction with 20 ml of ethyl acetate three times. The organic layers were combined together, washed with 10 ml of 10% HCl, 10 ml of a saturated $NaHCO_3$ solution and 20 ml of a saturated aqueous solution of common salt and dried over $Na_2SO_4$. The product was concentrated under reduced pressure to give 111 mg of a caramel, which was purified by to silica gel column chromatography (benzene/ethyl acetate=1:2) to give 98.0 mg of compound (B—XI-b) in the form of colorless prismatic crystals (yield: 94%). It was recrystallized from 1 ml of ethanol to give 90 mg (yield: 86%) of compound (B—XI-b) in the form of colorless prismatic crystals.

EXAMPLE 18

[Preparation of compound (C-II)]

119 g (0.57 mol) of compound (I) was dissolved in 285 ml (0.57 mol) of 2N NaOH. 90 ml (0.62 mol) of ZCl and 340 ml (0.68 mol) of 2N NaOH were separately added thereto dropwise over 30 min. After stirring under cooling with ice for 2 h, the product was washed with 100 ml of diethyl ether. The aqueous layer was acidified with concentrated hydrochloric acid under cooling with ice and then subjected to extraction with 1 l of ethyl acetate three times. The organic layers were combined, washed with a saturated NaCl solution and dried over $Na_2SO_4$. After concentration under reduced pressure, 187 g of compound (C-II) in the form of light brown powder was obtained (m.p.: 124° to 132° C.). It was recrystallized from benzene (1) / ethyl acetate (270 ml) to give 142 g (yield: 73%) of compound (C-II) in the form of a colorless powder.

Example 19

[Preparation of compound (C-III)]

2.17 ml 16.7 mmol) of isobutyl chloroformate was added to a solution of 5.0 g (14.6 mmol) of compound (C-II) and 2.33 ml (16.7 mmol) of triethylamine in 40 ml of $CH_2Cl_2$ under stirring at 0° C. The solution was stirred at 0° C. for 1.5 h and a solution of 1.82 ml (16.7 mmol) of benzylamine in 20 ml of $CH_2Cl_2$ was added dropwise thereto over 10 min. The reaction mixture was stirred at room temperature for 2.5 h.

80 ml of $CH_2Cl_2$ was added thereto and the mixture was successively washed with 40 ml of 10% HCl, 40 ml of a saturated $NaHCO_3$ solution and 40 ml of a saturated aqueous solution of common salt. The product was dried over $Na_2SO_4$ and concentrated under reduced pressure to give 6.72 g of compound (C-III) in the form of colorless acicular crystals (m.p.: 136° to 144° C.). The product was recrystallized from 48 ml of ethyl acetate to give 4.95 g (yield: 79%) of compound (C-III) in the form of colorless acicular crystals.

Example 20

[Preparation of compound [C-IV)]

70 ml of 25% $HBr/CH_3COOH$ was added to 7.02 g (16.2 mmol) of compound (C-III) and the mixture was stirred at room temperature for 12 h. After concentration under reduced pressure, 100 ml of water was added thereto and the aqueous solution was washed with 100 ml of diethyl ether three times. The pH of the aqueous layer was adjusted to around 10 with $Na_2CO_3$, and this layer was extracted with 100 ml of chloroform three times. The organic layers were combined together, washed with 100 ml of a saturated aqueous solution of common salt and dried over $Na_2SO_4$. The organic layer was concentrated at a reduced pressure to give 4.60 g (yield: 95%) of compound (C-IV) in the form of a yellow oil.

EXAMPLE 21

[Preparation of compound (C-V)]

A solution of 43.1 g (0.144 mol) of compound (C-IV) in 350 ml of THF was added dropwise to a suspension of 32.8 g (0.87 mol) of $LiAlH_4$ in 300 ml of THF at room temperature over 1 h. The resulting mixture was stirred under reflux for 61 h. 32 ml of water, 32 ml of 15% NaOH and 96 ml of water were successively added thereto under cooling with ice and the mixture was stirred for 30 min. An insoluble matter was filtered through Celite and the filtrate was concentrated under reduced pressure to give 33.5 g (yield: 82%) of compound (C-V) in the form of a yellow oil.

EXAMPLE 22

[Preparation of compound (C-VI)]

0.14 g (6.1 mmol) of Na was added to 4 ml of anhydrous ethanol. After Na had disappeared, 1.75 g (6.15 mmol) of compound (C-V) and a solution of 7.5 ml (61 mmol) of diethyl carbonate in 3 ml of ethanol were added thereto and the reaction mixture was stirred under reflux for 3.5 h. After cooling followed by concentration under reduced pressure, the pH of the solution was adjusted to around 1 with 10% HCl. The product was extracted with 20 ml of chloroform three times. The organic layers were combined, washed with a saturated aqueous solution of common salt and dried over $Na_2SO_4$. The organic layer thus treated was concentrated under reduced pressure to give 1.74 g of brown caramel, which was purified by to silica gel column chromatography (benzene/ethyl acetate=1:1) to give 1.65 g (yield: 87%) of the compound (C-VI) in the form of colorless acicular crystals. It was recrystallized from 50 ml of ethyl acetate/n-hexane (1:1) to give 1.33 g (yield: 70%) of the compound (C-VI) in the form of colorless acicular crystals.

EXAMPLE 23

[Preparation of compound (C-VII)]

40 mg (1.04 mmol) of NaH (60% suspension) was washed with 2 ml of anhydrous hexane three times and 2 ml of THF was added thereto. 125 mg (0.69 mmol) of compound (C-VI) was added thereto and the mixture was stirred under reflux for 2.5 h. After cooling, a solution of 199 mg (0.76 mmol) of 3,4,5-trimethoxybenzyl bromide in 2 ml of THF was added thereto and the resulting solution was stirred under reflux for 2 h. After cooling, 5 ml of a saturated $NH_4Cl$ solution was added thereto and the mixture was subjected to extraction with 10 ml of ethyl acetate three times. The ethyl acetate layers were successively combined, washed with 10 ml of 10% HCl, 10 ml of a saturated $NaHCO_3$ solution and 10 ml of a saturated aqueous solution of common salt and dried over $Na_2SO_4$. It was concentrated under reduced pressure to give 425 mg of a pale yellow oil. It was purified by to silica gel column chromatography (benzene / ethyl acetate=5:1) to give 330 mg (yield: 97%) of compound (C-VIII) in the form of colorless acircular crystals (m.p.: 114° to 117° C.). It was recrystallized from 1 ml of ethanol to give 300 mg (yield: 89%) of compound (C-VII) in the form of colorless acicular crystals.

EXAMPLE 24

[Preparation of compound (C-VIII-b)]

A solution of 495 mg (1.01 mmol) of compound (C-VII) in 20 ml of $CH_2Cl_2$ was added to a solution of 760 mg (6.06 mmol) of $VOF_3$ in a mixture of 1.5 ml of $CF_3COOH$ and 5 ml of $CH_2Cl_2$ at $-42°$ C. over 10 min. The reaction mixture was stirred at $-42°$ C. for 4 h and 20 ml of a saturated $Na_2CO_3$ solution was added thereto (pH $\approx$ 10). After extraction with 50 ml of $CH_2Cl_2$ three times, the organic layers were successively combined, washed with 40 ml of 10% HCl, 40 ml of water, 40 ml of a saturated $NaHCO_3$ solution and 40 ml of a saturated aqueous solution of common salt and dried over $Na_2SO_4$. The organic layer thus treated was concentrated under reduced pressure to give 470 mg of a brown oil, which was purified by to silica gel column chromatography (benzene/acetone=3:1) to give 429 mg (yield: 88%) of compound (C-VIII-b) in the form of colorless columnar crystals (m.p.: 143° to 147° C.). It was recrystallized from 1 ml of ethanol to give 380 mg (yield: 78%) of compound (C-VIII-b) in the form of colorless columnar or pillar crystals.

EXAMPLE 25

[Preparation of compound (C-IX)]

0.10 ml (0.82 mmol) of $(CH_3)_3SiCl$ (TMSCl) was added to 100 mg (0.204 mmol) of compound (C-VII) and a solution of 122 mg (0.82 mmol) of NaI in 0.8 ml of $CH_3CN$ and the reaction mixture was stirred at room temperature for 10 h. 1 ml of water was added thereto and the aqueous solution was stirred for 10 min and subjected to extraction with 15 ml of chloroform three times. The organic layers were combined, washed with 5 ml of a 10% $Na_2S_2O_2$ solution and 20 ml of a saturated aqueous solution of common salt and dried over $MgSO_4$. The organic layer thus treated was concentrated under reduced pressure to give 100 mg of a light brown oil, which was purified by to alumina column chromatography (chloroform/methanol=1:0→9:1) to give 32.1 mg (yield: 33%) of compound (C-IX).

The molecular formulae, molecular weights, melting points, and data of IR, NMR, MS and elementary analysis of the compounds prepared in the above-described Examples are summarized in Table 2.

EXAMPLE 26

(preparation of D-I-a and D-I-b)

One hundred ml of a benzene solution of 5.42 g (26 mmol) of the urethane compound (II), 5.57 g (28 mmol) of 3,4,5-trimethoxybenzaldehyde and 20 ml (260 mmol) of $CF_3COOH$ was stirred under reflux for 120 hours. After cooling, it was concentrated at a reduced pressure and then diluted with 70 ml of dichloromethane. The concentrated product was washed with 200 ml of sodium hydrogen carbonate and 200 ml of a saturated sodium hydroxide solution, and dried with sodium sulfate, to obtain 10.8 g of a light brown caramel. The caramel was purified by silica gel column chromatography of in a mixture of benzene and methyl acetate at a ratio changing from 3:1 to 1:2 to obtain 8.40 g of the trans body D-I-a of light yellow needle crystals and 0.54 g of the cis body D-I-b of light yellow needle crystals, with production yield of 80% and 5.5%, respectively. Then the cis-compound was re-crystallized from 5 ml of a mixture of chloroform and ether (1:1) to obtain 500 mg (yield of 4.8%) of colorless needle crystals.

EXAMPLE 27

(preparation of D-II and D-II')

Three grams (7.51 mmol) of the urethane compound D-I-b was dissolved in 24 ml of 1,2-dichloroethane. The solution was saturated with hydrogen bromide gas, while stirring at zero degree centigrade, followed by stirring at zero degree centigrade for 14 hours, and concentrated to obtain 3.1 g of oil. The oil was treated by silica gel column chlomatography using chloroform and acetone at a ratio changing rom 12:1 to 5:1 to obtain 2.31 g (yield of 80% of compound D-II in the form of white powder and then 290 mg (yield of 11%) of compound D-II' in the form of colorless prism crystals. These compounds were re-crystallized from acetone to obtain 2.19 g (yield of 76%) of white powder and 105 mg (yield of 4%) of colorless prism crystals, respectively.

EXAMPLE 28

(preparation of D-IV)

Twelve ml of an acetic acid suspension of 1.26 g (5.7 mmol) of the urethane compound II and 2.69 g (11.5 mmol) of 2,3-dichloro-5,6-dicyano-1,4-benzoquinone was heated and stirred at 60 degree centigrade for 50 hours. After concentration, it was diluted with 300 ml of methylene chloride and then washed with 100 ml of a saturated sodium carbonate, then 200 ml of 10% sodium hydroxide and 200 ml of a saturated saline. It was dried with magnesium sulfate, concentrated at a reduced pressure to obtain 1.29 of a mixture of the compounds II and D-III in the form of a brown caramel. 300 mg of the caramel was treated by silica gel column chromatography using dichloromethane and acetone at a ratio of 100:5 to separate compound II and obtain compound D-III in the form of the diastereomeric or enantiomic mixture at a ratio of 10:7. It was re-crystallized from chloroform and benzene to obtain colorless cylindrical crystals. 990 mg of compound D-III was dissolved in 36 ml of methanol and 532 mg (6.3 mmol) of sodium hydrogen carbonate was added thereto. The mixture was stirred at room temperature for 3 days. The reaction product was concentrated at a reduced pressure and treated with silica gel chromatography using chloroform and methanol at a ratio of 100:4 to obtain D-IV-1 and D-IV-2.

EXAMPLE 29

(preparation of D-V)

Sixty mg (0.26 mmol) of compound D-IV in benzene was treated with 1.5 ml of a concentrated hydrochloric acid. The benzene phase was washed with 5 ml of a saturated sodium hydrogen carbonate and 20 ml of a saturated sodium chloride, dried with sodium sulfate. The product was concentrated at a reduced pressure to obtain 58 mg (yield of 90%) of the diastereomer of the chlorinated compound.

EXAMPLE 30

(preparation of D-VI-a and D-VI-b)

Ten ml of a dimethylformamide solution of 58 mg (0.23 mmol) of compound D-V and 142 mg (0.76 mmol) of potassium phthalic imide was stirred at room temperature for 30 minutes and then at 40 degree centigrade for 30 minutes. It was diluted with 80 ml of chloroform and washed with 200 ml of water, 50 ml of 1% sodium hydroxide solution and 50 ml of a brine, dried with sodium sulfate. Having been concentrated at a reduced pressure, it was treated with silica gel column chromatography using dichloromethane and acetone at a ratio of 20:1 to obtain 57 mg (yield of 69%) of the first fraction D-VI-b in the form of colorless prism crystals and 24 mg (yield of 29%) of the second D-VI-a in the form of colorless oil.

EXAMPLE 31

(preparation of D-VII-a and D-VII-b)

Ten mg (0.027 mmol) of compound D-VI-a and 15 mg (0.07 mol) of 3,4,5-trimethoxybenzaldehyde were dissolved in 0.5 ml of a solvent mixture of methylene chloride and methanol at a mixing ratio of 10:1. To the solution was added 8.2 mg (0.05 mmol) of trifluoromethane sulfonic acid. The mixture was stirred at room temperature for 40 hours. It was diluted with methylene chloride and washed with 10 ml of a saturated aqueous solution hydrogen carbonate and 10 ml of a brine, dried with sodium sulfate. Concentrated at a reduced pressure, 27 mg of the obtained oil was treated with silica gel chromatography using dichloromethane and acetone at a ratio of 100:3 to obtain compound D-VII-a in the form of white powder. The same procedures as this gave compound D-VII-b in the form of colorless prism.

EXAMPLE 32

(preparation of D-XI-a and D-XI-b)

A methanol solution of 2.2 mg (0.004 mmol) of compound D-VIII-a and 0.01 ml (0.2 mmol) of hydrazin monohydrate was stirred at 40 degree centigrade for 1 hour. Ten ml of ethanol was added to the solution and the mixture was concentrated at a reduced pressure to obtain a white solid, which was dissolved in 0.1 ml of ethanol. 0.2 ml of 2N-hydrochloric acid was added thereto. The mixture was stirred and refluxed for 2 hours and concentrated at a reduced pressure. Two ml of 10% sodium hydroxide was added thereto. The organic phase obtained by extraction with 60 ml of methylene chloride was washed wit 20 ml of 10% sodium hydroxide and then 25 ml of a brine, dried with potassium carbonate. A white solid was obtained by concentration at a reduced pressure and treated by silica gel chromatography using chloroform and methanol at a ratio of 9:1 to obtain the amine compound D-VIII-a in the form of colorless needle crystals in the same way compound D-VIII-b of white powder was obtained from 54.2 g (0.1 mmol) of compound D-VII-b.

Apart from the above, 15 ml of a 1,4-dioxane solution of 161 mg (0.27 mmol) of the azide compound of D-X-a was stirred wit 247 mg of 5% Pd/CaCO3 as a catalyst in hydrogen gas at 30 degree centigrade for 10 hours. The reaction product was concentrated at a reduced pressure to obtain 182 mg of oil, which was treated with silica gel column chromatography using dichloromethane and methanol at a ratio of 100:3 to obtain the amino compound D-XI-a. The same way compound D-XI-b was obtained from D-X-b.

EXAMPLE 33

(preparation of D-X-a and D-X-b)

Four ml of a dimethylformaldehyde suspension of 127 mg (0.5 mmol) of the chlorinated compound of D-V and 97 mg (1.5 mmol) of NaN3 was stirred at 70 degree centigrade for 11 hours. The reaction product was diluted with chloroform and dried with sodium sulfate. It was concentrated at a reduced pressure to obtain 159 mg of oil, which was treated by silica gel chromatography using chloroform and acetone at a ratio of 10:1 to obtain the azide compound D-IX in the form of a diastereomer mixture. 25 mg (0.1 mmol) of the compound D-IX and 24 mg (0.12 mmol) of 3,4,5-trimethoxybenzaldehyde were dissolved in 1 ml of a solvent mixture of methylene chloride and methanol at a mixing ratio of 10:1. While being cooled with ice, 57 mg (0.38 mmol) of trifluoromethane sulfonic acid was added thereto. The mixture was stirred at room temperature for 24 hours. The reaction mixture was diluted with 50 ml of methylene chloride, washed with 20 ml of saturated sodium hydrogen carbonate and 20 ml of brine, and dried with sodium sulfate. It was then concentrated at a reduced pressure to obtain 57 mg of oil, which was treated by silica gel chromatography using dichloromethane and acetone at a ratio of 100:3 to obtain compounds D-X-a and D-X-b, both being colorless crystals.

Separately 54.2 mg (0.23 mmol) of D-IV was dissolved in 4 ml of 15% hydrochloric acid and methanol. The solution was stirred and refluxed for 1 hour and concentrated at a reduced pressure. The product was treated by silica gel column chromatography using dichloromethane and acetone at a ratio of 3:1 to obtain 57 mg (yield of 98%) of the methoxy compound of D-VIII in the form of a diastereomer mixture at a ratio of 1:1. 1.6 ml of a methylene chloride solution of 114 mg (0.45 mmol) of the methoxy compound and 62.7 mg (0.54 mmol) of (CH3)3SiN3 mixed with 101 mg (0.45 mmol) of CF 3SO3Si(CH3)3. The mixture was stirred at room temperature for 24 hours and refluxed for one more hour. After being cooled with ice, 0.12 g of KF and 6 ml of sodium hydrogen carbonate were added thereto and the mixture was stirred for 30 minutes. The reaction product was treated with 90 ml of methylene chloride for extraction. The extract was washed with 30 ml of saturated sodium hydrogen carbonate and 30 ml of brine. It was concentrated at a reduced pressure to obtain 145 mg of oil, which was treated by silica gel column chromatography using hexane and ethyl acetate at a mixing ratio of 2:3 for isolation of D-IX.

TABLE 2

| Compound | Molecular formula | Molecular weight | Melting point (°C.) | IR (cm$^{-1}$) | NMR δ(CDCl$_3$) | MS M+ | Elementary analysis calcd. (%) | found (%) |
|---|---|---|---|---|---|---|---|---|
| II | C$_{11}$H$_{11}$O$_4$N | 221.21 | 82.0~83.5 | 3230, 3145, 1755 (C=O), 1025, 915 (Nujol) | 2.78(2H, d, J=6Hz), 3.82~4.62(3H, m), 5.54(1H, bs), 5.95(2H, s), 6.49~6.92(3H, m) | 221 | C 59.73<br>H 5.01<br>N 6.33 | 60.01<br>5.01<br>6.16 |
| A-III | C$_{21}$H$_{23}$O$_7$N | 401.42 | 94.5~96.5 | 1737 (KBr) | 2.59(1H, dd, J=8Hz, 14Hz), 3.03(1H, dd, J=5Hz, 14Hz), 3.85(9H, s), 3.6~4.3(3H, m), 4.01, 4.78(each 1H, d, J=15Hz), 5.94(2H, s), 6.4~6.8(5H, m) | 401 | C 62.83<br>H 5.77<br>N 3.49 | 62.97<br>5.75<br>3.66 |
| A-IV-b | C$_{21}$H$_{21}$O$_7$N | 399.40 | 185~186 | 1735 (KBr) | 2.48(1H, dd, J=9.9Hz, 13.7Hz), 2.63(1H, d, J=13.7Hz), 3.36(1H, d, J=14.3Hz), 3.63, 3.90, 3.91(each 3H, s) 3.72~3.88(2H, m), 4.50~4.56(1H, m) 4.64(1H, d, J=14.3Hz), 6.01, 6.04(each 1H, d, J=1.5Hz), 6.72, 6.76, 6.99(each 1H, s) | 399 | C 63.15<br>H 5.30<br>N 3.51 | 62.96<br>5.34<br>3.60 |
| A-IV-a | C$_{21}$H$_{21}$O$_7$N | 399.40 | 167~168 | 1737 (KBr) | 2.43(1H, dd, J=2.0Hz, 14.3Hz), 2.89(1H, dd, J=6.6Hz, 14.3Hz), 3.54, 3.89, 3.90(each 3H, s), 4.0(1h, m), 4.09(1H, d, J=14.7Hz), 4.09(1H, dd, J=5.7Hz, 8.9Hz), 4.40(1H, dd, J=8.6Hz, 8.9Hz), 4.78(1H, d, J=14.7Hz), 5.98(1H, d, J=1.5Hz), 6.02(1H, d, J=1.5Hz), 6.59, 6.71, 6.77(each 1H, s) | 399 | C 62.22<br>H 5.39<br>N 3.45<br>(as hemihydrate) | 62.13<br>5.21<br>3.34 |
| A-V-b | C$_{21}$H$_{25}$O$_6$N | 387.43 | 88~90 | 3400 (KBr) | 2.31(3H, s), 2.2~2.6(3H, m), 2.60(1H, s), 3.28, 3.56(each 1H, d, J=13Hz), 3.4~3.8(2H, m), 3.53(3H, s), 3.86(6H, s), 5.91, 5.94(each 1H, d, J=1Hz), 6.68(2H, s), 6.72(1H, s) | 387 | C 67.69<br>H 6.51<br>N 3.29<br>(as ¼ C$_6$H$_5$) | 67.48<br>6.78<br>3.26 |
| A-VI-a | C$_{23}$H$_{27}$O$_7$N | 429.47 | 199~201 (hydrochloride) | 1740 (CHCL$_3$) | 2.08(3H, s), 2.32(3H, s), 2.4~2.5(2H, m), 2.67(1H, m), 3.21, 3.54(each 1H, d, J=13Hz), 3.54(3H, s), 3.87(6H, s), 3.91(1H, dd, J=7Hz, 11Hz), 4.24(1H, dd, J=5Hz, 11Hz), 5.92, 5.95(each 1H, d, J=1Hz), 6.65, 6.67, 6.75(each 1H, s) | 429 | C 59.29<br>H 6.06<br>N 3.01<br>(as hydrochloride) | 59.54<br>6.14<br>3.05 |
| A-VII-a | C$_{21}$H$_{23}$O$_7$N | 401.40 | colorless oil | 3380, 1658 (CHCl$_3$) | 2.58(1H, dd, J=3Hz, 15Hz), 2.99(1H, dd, J=5Hz, 15Hz), 3.17(1H, d, J=15Hz), | 401 | 401.1472<br>(high resoln M.S.) | 401.1454 |

TABLE 2-continued

| Compound | Molecular formula | Molecular weight | Melting point (°C.) | IR (cm$^{-1}$) | NMR δ(CDCl$_3$) | MS M$^+$ | Elementary analysis | calcd. (%) | found (%) |
|---|---|---|---|---|---|---|---|---|---|
| A-VIII-b | $C_{20}H_{19}O_7N$ | 385 | 239~242 | 3360, 1713 (CHCl$_3$) | 3.56, 3.88, 3.89(each 3H, s), 3.4~4.2(4H, m), 4.98(1H, d, J=15Hz), 5.97, 6.00(each 1H, d, J=1Hz), 6.6~6.9(2H, m), 7.14(1H, s), 8.12(1H, s) 2.39(1H, d, J=14Hz), 2.59(1H, dd, J=3Hz, 14Hz), 3.29, 4.57(each 1H, d, J=14Hz), 3.47, 3.90(each 3H, s), 3.68~3.96(2H, m), 4.48(1H, dd, J=12Hz, 12Hz), 5.63(1H, bs), 5.95, 5.98(each 1H, d, J=1Hz), 6.67, 6.72, 6.91(each 1H, s) | 385 | C H N | 62.33 4.97 3.63 | 62.06 4.92 3.41 |
| A-IX-b | $C_{20}H_{19}O_7N$ | 385 | colorless oil | 3518, 1743 (CHCl$_3$) | 2.50(1H, dd, J=9.3Hz, 13.7Hz), 2.63(1H, d, J=13.7Hz), 3.36, 4.63(each 1H, d, J=14.3Hz), 3.83~3.87(2H, m), 3.92, 3.95(each 3H, s), 4.53(1H, dd, J=13.2Hz, 13.2Hz), 5.89(1H, bs), 6.02(2H, s), 6.74, 6.81, 6.85(each 1H, s) | 385 | | 385.1162 (high resoln M.S.) | 385.1207 |
| B-II | $C_{20}H_{21}O_8N$ | 403.39 | 190~193 | 1705, 1627 (KBr) | 3.07(1H, dd, J=8Hz, 13Hz), 3.29(1H, dd, J=5Hz, 13Hz), 3.81(3H, s), 3.85(6H, s), 5.22(1H, dd, J=5Hz, 8Hz), 5.88(2H, s), 6.7~6.8(3H, m), 7.05(2H, s) solvent: CD$_3$COOD | 403 | C H N | 59.55 5.25 3.47 | 59.79 5.27 3.71 |
| B-III | $C_{20}H_{22}O_7N$ | 402.41 | 218~220 | 1680, 1637 (KBr) | 2.99(1H, dd, J=9Hz, 13Hz), 3.17(1H, dd, J=6Hz, 13Hz), 3.80(3H, s), 3.86(6H, s), 5.02(1H, dd, J=6Hz, 9Hz), 5.87(2H, s), 6.7~6.8(3H, m), 7.09(2H, s) solvent: CD$_3$COOD | 402 | C H N | 59.70 5.51 6.96 | 59.40 5.54 7.04 |
| B-IV | $C_{20}H_{26}O_5N_2$ | 374.44 | 211~213 (as picrate) | 3370 (neat) | 1.64(3H, s), 2.72(5H, bs), 3.73(2H, s), 3.83(9H, s), 5.93(2H, s), 6.47(2H, s), 6.67(2H, s) | 375 (M$^+$+1) | C H N | 46.16 3.87 13.46 (as picrate) | 46.22 3.90 13.53 |
| B-V | $C_{21}H_{24}O_6N_2$ | 400.43 | oil | 1700 (neat) | 2.54(1H, dd, J=9Hz, 14Hz), 2.99(1H, d, J=14Hz), 2.9~3.4(2H, m), 3.66(1H, m), 3.83(9H, s), 3.96, 4.76(each 1H, d, J=15Hz), 4.77(1H, s), 5.89(2H, s), 6.4~6.7(5H, m) | 400 | C H N | 62.99 6.04 7.00 | 62.99 6.28 6.72 |
| B-VI-b | $C_{21}H_{22}O_6N_2$ | 398.42 | 236~237 | 1700 (KBr) | 1.66(1H, bs), 2.49(1H, dd, J=10.1Hz, 13.7Hz), 2.62(1H, d, J=13.7Hz), 3.05(1H, dd, J=8.6Hz, 8.6Hz), 3.19, 4.69(each 1H, d, J=14.3Hz), 3.62(1H, m), 3.62, 3.90, 3.91(each 3H, s), 3.75(1H, m), 6.00, 6.01(each 1H, d, J=1.5Hz), 6.73, 6.76, 6.97(each 1H, s) | 398 | C H N | 63.31 5.57 7.03 | 63.09 5.54 6.97 |
| B-VII-b | $C_{27}H_{32}O_8N_2$ | 512.56 | 117.5~119 | 1732, 1683 (KBr) | 1.42(9H, s), 2.49~2.59(2H, m), 3.04~3.18(2H, m), 3.21, 4.71(each 1H, d, J=14Hz), 3.60(3H, s), 3.67~3.70(1H, m), 3.90(6H, s), 3.85, 3.87(each 1H, s), 5.99, 6.02(each 1H, d, J=1Hz), 6.73, 6.76, 6.97(each 1H, s) | 512 | C H N | 63.27 6.29 5.47 | 63.01 6.28 5.23 |
| B-VIII-b | $C_{23}H_{24}O_8N_2$ | 456.46 | 256~257 | 1745, 1635 (KBr) | 2.3~2.8(2H, m), 3.1~3.2(2H, m), 3.26~4.68(each 1H, d, J=14Hz), 3.56(3H, s), 3.74(1H, m), 3.87(6H, s), 3.78, 4.07(each 1H, d, J=4Hz), 5.97, 6.00(each 1H, s), 6.73, 6.82, 6.99(each 1H, s) solvent: CD$_3$COOD | 456 | C H N | 60.52 5.30 6.14 | 60.38 5.26 6.06 |
| B-X-b | $C_{23}H_{24}O_7N_2$ | 440.46 | 197~198 | 1718, 1668 (KBr) | 2.46(1H, dd, J=10.6Hz, 13.6Hz), 2.52(3H, s), 2.70(1H, d, J=13.6Hz), 3.28, 4.74(each 1H, d, J=14.1Hz), 3.33(1H, dd, J=7.7Hz, 11.7Hz), 3.61(3H, s), 3.67(1H, m), 3.96, 4.10(each 3H, s), 4.14(1H, dd, J=9.3Hz, 11.7Hz), 6.01, 6.04(each 1H, d, J=1.5Hz), | 440 | C H N | 62.72 5.49 6.36 | 62.89 5.55 6.36 |

TABLE 2-continued

| Compound | Molecular formula | Molecular weight | Melting point (°C.) | IR (cm$^{-1}$) | NMR δ(CDCl$_3$) | MS M$^+$ | Elementary analysis calcd. (%) | found (%) |
|---|---|---|---|---|---|---|---|---|
| B-IX-b | $C_{25}H_{26}O_7N_2$ | 466.49 | 241~243 | 1703, 1667, 1630 (KBr) | 6.758, 6.762, 6.96(each 1H, s) 1.88(3H, dd, J=1Hz, 6Hz), 2.38(1H, dd, J=10Hz, 14Hz), 2.66(1H, dd, J=1Hz, 14Hz), 3.21, 4.69(each 1H, d, J=14Hz), 3.2~3.9(2H, m), 3.56, 3.84, 3.86(each 3H, s), 4.12(1H, dd, J=9Hz, 11Hz), 5.93, 5.96(each 1H, d, J=1Hz), 6.69(2H, s), 6.88(1H, s), 6.9~7.4(2H, m) | 466 | C 64.37<br>H 5.62<br>N 6.01 | 64.10<br>5.71<br>5.97 |
| C-II | $C_{18}H_{17}O_6N$ | 343.34 | 143.5~144.5 | 1708, 1680 (KBr) | 3.06(2H, bd, J=6Hz), 4.64(1H, m), 5.09(2H, s), 5.20(1H, bs), 5.91(2H, s), 6.5~6.7(3H, m), 7.32(5H, s), 9.92(1H, s) | 343 | C 62.97<br>H 4.99<br>N 4.08 | 62.75<br>4.97<br>4.14 |
| C-III | $C_{25}H_{24}O_5N_2$ | 432.48 | 151~152 | 1697, 1655 (KBr) | 2.86(1H, dd, J=8Hz, 14Hz), 3.11(1H, dd, J=5Hz, 14Hz), 4.27(1H, m), 4.35(2H, d, J=6Hz), 5.06(2H, s), 5.28(1H, bd), 5.91(2H, s), 5.95(1H, bs), 6.5~6.7(3H, m), 7.0~7.3(10H, m) | 432 | C 69.43<br>H 5.59<br>N 6.48 | 69.15<br>5.55<br>6.37 |
| C-IV | $C_{18}H_{18}O_3N_2$ | 298.34 | oil 193~194 (as picrate) | 3320, 1660 (neat) | 1.71(2H, s), 2.71(1H, dd, J=9Hz, 14Hz), 3.15(1H, dd, J=4Hz, 14Hz), 3.61(1H, dd, J=4Hz, 9Hz), 4.46(2H, d, J=6Hz), 5.91(2H, s), 6.70(3H, m), 7.26(5H, s), 7.58(1H, bd, J=6Hz) | 298 | C 52.38<br>H 4.01<br>N 13.28<br>(as picrate) | 52.56<br>4.01<br>13.40 |
| C-V | $C_{18}H_{20}O_2N_2$ | 284.36 | 127~129 (as picrate) | 3375 (neat) | 1.68(3H, s), 2.2~2.8(4H, m), 3.03(1H, m), 3.78(2H, s), 5.91(2H, s), 6.5~6.8(3H, m), 7.28(5H, s) | 285 (M$^+$+1) | C 47.21<br>H 4.09<br>N 14.21<br>(as picrate ethanol) | 47.42<br>4.08<br>14.20 |
| C-VI | $C_{18}H_{18}O_3N_2$ | 310.35 | 111~112 | 3240, 1680 (KBr) | 2.68(2H, bd, J=7Hz), 2.99(1H, dd, J=6Hz, 9Hz), 3.33(1H, dd, J=9Hz, 9Hz), 3.78(1H, m), 4.35(2H, s), 4.6(1H, bs), 5.91(2H, s), 6.5~6.8(3H, m), 7.28(1H, bs) | 310 | C 69.66<br>H 5.85<br>N 9.03 | 69.54<br>5.86<br>8.85 |
| C-VII | $C_{28}H_{30}O_6N_2$ | 490.56 | 116~117 | 1660 (KBr) | 2.48(1H, dd, J=9Hz, 14Hz), 2.91(1H, d, J=14Hz) 2.77~3.16(2H, m), 3.48(1H, m), 3.84(9H, s), 3.6~4.6(2H, m), 3.99, 4.84(each 1H, d, J=15Hz), 5.89(2H, s), 6.39~6.69(5H, m), 7.21(5H, bs) | 490 | C 68.56<br>H 6.16<br>N 5.71 | 68.32<br>6.17<br>5.71 |
| C-VIII-b | $C_{28}H_{28}O_6N_2$ | 488.54 | 146~147.5 | 1685 (KBr) | 2.28~2.84(3H, m), 3.20, 4.75(each 1H, d, J=15Hz), 3.32~3.54(2H, m), 3.60, 3.91, 3.93(each 1H, s), 4.08, 4.64(each 1H, d, J=15Hz), 5.97, 6.00(each 1H, d, J=1Hz), 6.66, 6.74, 6.99(each 1H, s), 7.26(5H, bs) | 488 | C 68.84<br>H 5.78<br>N 5.73 | 68.67<br>5.79<br>5.83 |
| C-IX | $C_{27}H_{28}O_6N_2$ | 476.53 | colorless oil | 3535, 1685 1618 (CHCl$_3$) | 2.40(1H, dd, J=9Hz, 14Hz), 2.70~3.09(3H, m), 3.82(6H, s), 3.91, 4.80(each 1H, d, J=15Hz), 4.12, 4.42(each 1H, d, J=15Hz), 5.41(1H, bs), 5.84(2H, s), 6.33~6.64(5H, m), 7.17(1H, bs) | 476 | 476.1944 (high resoln M.S.) | 476.1929 |
| D-III | $C_{13}H_{13}O_6N$ | 279.25 | 177~179 | 3450, 1764 1750 (CHCl$_3$) | 2.12(3H, s), 4.07(1H, dd, J=5.1Hz, 8.8Hz), 4.1~4.2(1H, m), 4.26(1H, dd, J=8.4Hz, 8.8Hz), 5.57(1H, d, J=8.0Hz), 5.97, 5.98(each 1H, d, J=1.5Hz), 6.28(1H, brs), 6.79~6.84(3H, m) | 279 | C 55.91<br>H 4.69<br>N 5.02 | 55.83<br>4.72<br>4.97 |
| D-IV-1 | $C_{11}H_{11}O_5N$ | 237.21 | 120~121 | 3310, 1743 (KBr) | 2.1(1H, brs), 3.98(1H, ddd, J=5.5Hz, 8.1Hz, 9.0Hz), 4.07(1H, dd, J=5.5Hz, 9.0Hz), 4.21(1H, dd, J=9.0Hz), 4.52(1H, d, J=8.1Hz), 5.85(1H, brs), 5.99(2H, s), 4.21(1H, dd, J=9.0Hz), 6.78~6.87(3H, m), | 237 | C 55.70<br>H 4.67<br>N 5.90 | 55.41<br>4.67<br>5.69 |
| D-IV-2 | | | | | 2.0(1H, brs), 3.92~4.00(1H, m), 4.43(1H, dd, J=7.7Hz, 9.2Hz), 4.45(1H, dd, J=5.9Hz, 9.2Hz), 4.60(1H, d, J=6.6Hz), 5.23(1H, | | | |

TABLE 2-continued

| Compound | Molecular formula | Molecular weight | Melting point (°C.) | IR (cm$^{-1}$) | NMR δ(CDCl$_3$) | MS M$^+$ | Elementary analysis | calcd. (%) | found (%) |
|---|---|---|---|---|---|---|---|---|---|
| D-V | C$_{11}$H$_{10}$O$_4$NCl | 255.66 | oil | 1750 (KBr) | brs), 5.99(2H, s), 6.77~6.87(3H, m) 4.19~4.30(1H, m), 4.43(1H, dd, J=4.8Hz, 9.5Hz), 4.58(1H, dd, J=8.2Hz, 9.5Hz), 4.67(1H, d, J=8.8Hz), 5.54(1H, brs), 6.00(2H, s), 6.78~6.87(3H, m) | 255 | C H N | | |
| D-VI-a | C$_{19}$H$_{14}$O$_6$N$_2$ | 366.33 | 251~252.5 | 1750, 1707 (KBr) | 4.06(1H, dd, J=4.6Hz, 9.2Hz), 4.39(1H, dd, J=8.4Hz, 9.2Hz), 5.14(1H, d, J=10.6Hz), 5.74(1H, brs), 5.94, 5.95(each 1H, d, J=1.5Hz), 6.76~6.78(1H, m), 6.98~7.05(2H, m), 7.71~7.85(4H, m) | 366 | C H N | 62.30 3.85 7.65 | 62.36 3.87 7.70 |
| D-I-a (trans) | C$_{21}$H$_{21}$O$_7$N | 399.1316 | 194.0~194.5 | 1725, 1592 (KBr) | 2.87(1H, d, J=15.4Hz), 2.93(1H, dd, J=5.1Hz, 15.4Hz), 3.80(6H, s), 3.84(3H, s), 4.03(1H, m), 4.11(1H, dd, J=4.2Hz, 8.4Hz), 4.48(1H, dd, J=8.4Hz), 5.85(1H, s) 5.94, 5.97(each 1H, d, J=1.5Hz), 6.46(1H, s), 6.47(2H, s), 6.64(1H, s) | 399 | C H N | 63.15 5.30 3.51 | 62.87 5.25 3.59 |
| D-I-b (cis) | C$_{21}$H$_{21}$O$_7$N | 399.1285 | 248~250 | 1740, 1592 (KBr) | 2.96(1H, dd, J=3.7Hz, 14.5Hz), 3.02(1H, d, J=14.5Hz), 3.80(3H, s), 3.82(6H, s), 4.05(1H, dd, J=7.0Hz, 11.0Hz), 4.12(1H, m), 4.55(1H, dd, J=7.0Hz, 7.1Hz), 5.49(1H, s), 5.90, 5.93(each 1H, d, J=0.7Hz), 6.50(2H, s), 6.53, 6.62(each 1H, s) | 399 | C H N | 62.22 5.39 3.45 as ¼ hydrate | 62.34 5.28 3.36 |
| D-II | C$_{20}$H$_{19}$O$_7$N | 385.38 | 210~212 | 3530, 1743 1613 (CHCl$_3$) | 2.86(1H, d, J=15.4Hz), 2.93(1H, dd, J=5.1Hz, 15.4Hz), 3.83(6H, s), 4.03(1H, m), 4.10(1H, dd, J=4.4Hz, 8.4Hz), 4.46(1H, dd, J=8.4Hz, 5.53(1H, Br), 5.85(1H, s), 5.93, 5.96(each 1H, d, J=1.3Hz), 6.46(1H, s), 6.48(2H, s), 6.63(1H, s) | 385 | C H N | 62.33 4.97 3.63 | 62.17 4.93 3.67 |
| D-II' | C$_{20}$H$_{19}$O$_7$N | 385.38 | 226.5~228 | 3280, 1724 (KBr) | 2.83~2.91(2H, m), 3.88(3H, s), 4.08(1H, m), 4.08(1H, dd, J=4.0Hz, 9.6Hz), 4.46(1H, dd, J=9.6Hz), 5.38, 5.43(each 1H, s), 5.82(1H, s), 5.93(2H, s), 6.23, 6.66(each 1H, d, J=2.0Hz), 6.44, 6.61(each 1H, s) | 371 | C H N | 61.45 4.61 3.77 | 61.25 4.62 3.69 |
| D-VI-b | C$_{19}$H$_{14}$O$_6$N$_2$ | 366.33 | oil | 3445, 1769 1712 (CHCl$_3$) | 4.16(1H, dd, J=4.0Hz, 9.2Hz), 4.53(1H, dd, J=7.7Hz, 9.2Hz), 5.11~5.18(2H, m), 5.45(1H, brs), 5.93, 5.94(each 1H, d, J=1.5Hz) 6.77~6.79(1H, m), 6.97~7.05(2H, m), 7.72~7.84(4H, m) | 366 | C H N | 61.54 3.94 7.55 as ¼ hydrate | 61.54 3.82 7.36 |
| D-VII-a | C$_{29}$H$_{24}$O$_9$N$_2$ | 544.52 | 315~316 (decomposed) | 1750, 1720 (CHCl$_3$) | 3.83(6H, s), 3.86(3H, s), 4.11~4.12(1H, m), 4.41(1H, d, J=8.8Hz), 4.44(1H, dd, J=2.2Hz, 8.8Hz), 5.44(1H, d, J=3.3Hz), 5.90, 5.97(each 1H, d, J=1.5Hz), 6.13(1H, s), 6.54(1H, s), 6.58(2H, s), 6.61(1H, s), 7.75~7.90(4H, m) | 544 | C H N | | |
| D-VII-b | C$_{29}$H$_{24}$O$_7$N$_2$ | 544.52 | 267~268 | 1760, 1712 (KBr) | 3.86(3H, s), 3.91(6H, s), 4.24(1H, dd, J=3.7Hz, 8.8Hz), 4.35(1H, dd, J=8.1Hz, 8.8Hz), 4.65(1H, ddd, J=3.7Hz, 8.1Hz, 9.9Hz), 5.48(1H, d, J=9.9Hz), 5.92, 5.93(each 1H, d, J=1.5Hz), 5.94(1H, s), 6.42, 6.52(each 1H, s), 6.76(2H, s), 7.81~7.83(2H, m), 7.93(2H, brs) | 544 | C H N | 63.97 4.44 5.14 | 63.99 4.40 5.10 |
| D-X-a | C$_{21}$H$_{20}$O$_4$N$_7$ | 440.42 | 199.5~200.5 | 2100, 1752 (CHCl$_3$) | 3.80(6H, s), 3.84(3H, s), 4.20(1H, ddd, J=2.6Hz, 4.0Hz, 8.8Hz), 4.37(1H, d, J=2.6Hz), 4.41(1H, dd, J=8.8Hz), 4.55(1H, dd, J=4.0Hz, 8.0Hz), 5.90(1H, s), 6.02, 6.05(each 1H, d, J=1.1Hz), 6.45(2H, s), 6.55, 6.79(each 1H, s) | 440 | C H N | 57.27 4.58 12.72 | 57.39 4.60 12.66 |
| D-X-b | C$_{21}$H$_{20}$O$_4$N$_7$ | 440.42 | 174~175 | 2100, 1755 | 3.78(6H, s), 3.84(3H, s), | 440 | C | 57.27 | 57.30 |

TABLE 2-continued

| Compound | Molecular formula | Molecular weight | Melting point (°C.) | IR (cm$^{-1}$) | NMR δ(CDCl$_3$) | MS M$^+$ | Elementary analysis | calcd. (%) | found (%) |
|---|---|---|---|---|---|---|---|---|---|
| | | | | (CHCl$_3$) | 3.92(1H, ddd, J=4.0Hz, 8.1Hz, 9.5Hz), 4.30(1H, d, J=9.5Hz), 4.36(1H, dd, J=4.0Hz, 9.2Hz), 4.57(1H, dd, J=8.1Hz, 9.2Hz), 5.87(1H, s), 6.01, 6.04(each 1H, d, J=1.1Hz), 6.43(2H, s), 6.50, 7.03(each 1H, s) | | H | 4.58 | 4.56 |
| | | | | | | | N | 12.72 | 12.73 |
| D-XI-a | C$_{21}$H$_{22}$O$_7$N$_2$ | 414.41 | 261~263 (decomposed) | 3400, 1737 (KBr) | 1.94(2H, brs), 3.79(1H, d, J=2.9Hz), 3.80(6H, s), 3.84(3H, s), 4.14(1H, ddd, J=2.9Hz, 4.0Hz, 8.8Hz), 4.41(1H, dd, J=8.8Hz), 4.63(1H, dd, J=4.0Hz, 8.8Hz), 5.86(1H, s), 5.95, 5.99(each 1H, d, J=1.5Hz), 6.46(2H, s), 6.45, 6.77(each 1H, s) | 414 | C H N | 55.94 5.14 6.21 | 55.65 5.07 5.98 |
| D-XI-b | C$_{21}$H$_{22}$O$_7$N$_2$ | 414.41 | 203~205 | 3340, 1730 (CHCl$_3$) | 1.61(2H, s), 3.56(1H, ddd, J=3.7Hz, 8.1Hz, 9.9Hz), 3.75(1H, d, J=9.9Hz), 3.80 (6H, s), 3.84(3H, s), 4.42(1H, dd, J=3.7Hz, 9.0Hz), 4.50(1H, dd, J=8.1Hz, 9.0Hz), 5.84(1H, s), 5.96, 5.99(each 1H, d, J=1.5Hz), 6.44(1H, s), 6.48(2H, s), 7.14(1H, s) | 414 | C H N | 55.94 5.14 6.21 | 55.78 5.41 6.13 |

We claim:

1. An azacyclooctadiene compound having the following formula (2) or a pharmacologically acceptable salt thereof:

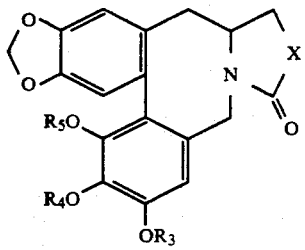

(2)

in which R$_3$, R$_4$ and R$_5$ are each hydrogen or methyl and X is oxygen or —NZ—, with Z being hydrogen, methyl, —COOH$_3$, —CH$_2$COOH, —CO—CH=CH$_2$, —CO—CH=CH—CH$_3$, —CH$_2$C$_6$H$_5$, —CH$_2$OH, —CH$_2$OCOCH$_3$ or —CH$_2$COOC(CH$_3$)$_3$.

2. The azacyclooctadiene compound or pharmacologically acceptable salt thereof as claimed in claim 1, in which X is oxygen.

3. The azacyclooctadiene compound or pharmacologically acceptable salt thereof as claimed in claim 1, in which R$_3$, R$_4$ and R$_5$ are all methyl and X is oxygen.

4. The azacyclooctadiene compound or pharmacologically acceptable salt thereof as claimed in claim 1, in which R$_3$ is hydrogen, R$_4$ and R$_5$ are methyl and X is oxygen.

5. A pharmacological composition which comprises a therapeutically effective amount of the azacyclooctadiene compound or pharmacologically acceptable salt thereof as defined in claim 1 to inhibit the growth of tumor cells, and a pharmacologically acceptable carrier.

* * * * *

UNITED STATES PATENT AND TRADEMARK OFFICE
CERTIFICATE OF CORRECTION

PATENT NO. : 5 075 296

DATED : December 24, 1991

INVENTOR(S) : Kenji Koga et al

It is certified that error appears in the above-identified patent and that said Letters Patent is hereby corrected as shown below:

On the Title page, in Abstract, second to last line; change "being —SC—" to ---being —CS— ---.

Column 41, line 46; change "methyl, —COOH$_3$," to ---methyl, —COCH$_3$,---.

Signed and Sealed this

Twenty-fifth Day of May, 1993

Attest:

Attesting Officer

MICHAEL K. KIRK

Acting Commissioner of Patents and Trademarks